(12) United States Patent
McNeil

(10) Patent No.: US 6,429,016 B1
(45) Date of Patent: Aug. 6, 2002

(54) SYSTEM AND METHOD FOR SAMPLE POSITIONING IN A ROBOTIC SYSTEM

(75) Inventor: John McNeil, La Jolla, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/411,748

(22) Filed: Oct. 1, 1999

(51) Int. Cl.[7] .............................................. G01N 35/04

(52) U.S. Cl. ............................ 436/47; 436/43; 436/49; 436/50; 436/164; 422/63; 422/65; 422/67; 701/24; 701/25; 701/26; 701/200; 701/205; 701/300; 701/301; 414/222.02

(58) Field of Search ............................ 422/63, 65, 67, 422/66, 100, 104; 436/43, 47, 49, 50, 164, 180; 701/24, 25, 26, 200, 205, 300, 301; 414/222.01

(56) References Cited

U.S. PATENT DOCUMENTS

| | | | | |
|---|---|---|---|---|
| 4,692,308 A | * | 9/1987 | Riley et al. | 422/65 |
| 5,149,654 A | | 9/1992 | Gross et al. | 435/287 |
| 5,283,739 A | * | 2/1994 | Summerville et al. | 364/424.02 |
| 5,307,271 A | * | 4/1994 | Everett, Jr. | 364/424.02 |
| 5,323,098 A | * | 6/1994 | Hamaguchi et al. | 320/2 |
| 5,329,449 A | * | 7/1994 | Tanizawa et al. | 364/424.02 |
| 5,350,564 A | * | 9/1994 | Massa et al. | 422/63 |
| 5,402,051 A | * | 3/1995 | Fujiwara et al. | 318/587 |
| 5,446,356 A | * | 8/1995 | Kim | 318/587 |
| 5,623,415 A | * | 4/1997 | O'Bryan et al. | 364/478.13 |
| 5,758,298 A | * | 5/1998 | Guldner | 701/23 |
| 5,985,214 A | * | 11/1999 | Stylli et al. | 422/65 |
| 6,132,685 A | * | 10/2000 | Kercso et al. | 422/104 |
| 6,177,050 B1 | * | 1/2001 | Bybee et al. | 422/65 |
| 6,202,024 B1 | * | 3/2001 | Yokoyama et al. | 701/207 |

OTHER PUBLICATIONS

Website: //www.lbl.gov/Tech–Transfer/techs/lbnl1114.html "Prep Track: Assembly Line Automation of Microtiter Plate Biochemistry" (1 page)– printout of Sep. 14, 1999.

Website: //www.hgighub.lbl.gov/esd/BioinstrGroup/Prep Track Webpage/preptrack.htm, "Prep Track" (2 pages)—printout of Sep. 14, 1999.

Tony A.D. Hansen et al. "Modular, Continuous–Throughput System for Processings Biochemical Samples in Microtiter Plates" Website: //www–hgc.lbl.gov/instr/hansen.html (1 page)—printout of Sep. 14, 1999.

Martin J. Pollard "Lawrence Berkely Laboratory DNA Preparation Machine" Website: //www.ornl.gov/TechResources/Human Genome/publicat/94santa/instrum.../pollard1.htm (1 page)– printout of Sep. 14, 1999.

(List continued on next page.)

*Primary Examiner*—Jill Warden
*Assistant Examiner*—Kathryn Bex
(74) *Attorney, Agent, or Firm*—Woodcock Washburn LLP

(57) ABSTRACT

A system and method for positioning a sample, or cargo, with respect to a device in a robotic system is provided. The system includes a macro positioning system for "gross" movement of the sample between stations and a micro positioning system for precisely locating the sample in a predetermined location at a station with respect to a device that will interact with the sample. The macro positioning system provides a positioning mechanism for the general movement of a sample along a pathway between various destinations or stations wherein the sample is "grossly" positioned with respect to the station. Once at the station, the micro positioning subsystem disposed between a sample carrier and the station provides a positioning mechanism for "precisely" positioning the sample in a predetermined location at the station with respect to a device that will interact with, or perform some function on, the sample. The system and method provide for multiple sample carrying robots having autonomous navigation thereby providing flexibility and stacker-like queuing for near 100% device utilization.

31 Claims, 25 Drawing Sheets

OTHER PUBLICATIONS

John Meng et al. Turbo PCR—An Integrated Robotic System for Continuously Setting Up and Running Multiple PCR Reactions Website: //www.ornl.gov/TechResources/Human Genome/publicat/94santa/instrument.../meng.htm, (1 page)– printout of Sep. 14, 1999.

Website: //www.nidatech.com/workst.htm, Nidatech, "Liquid Handl.System" (1 page)—printout of Sep. 17, 1999.

Website: //www.nidatech.com/multi/htm, Nidatech, "Multi Chan. Pipettes" (1 page)– printout of Sep. 17, 1999.

Website://www.nitdatech.com/8chan.htm,Nidatech, "8 Chan Pipettes" (1 page).

Website://www.nidatech.com/washer.htm, Nidatech, "Mini-Washers" Sep. 17, 1999 (1 page)– printoout of Sep. 17, 1999.

Website: //www.nidatech.com/fmpipette.htm, Nidatech, "FM Pipette" (3 pages— printout of Sep. 17, 1999.

Website: //www.nidatech.com/fillmaster.htm, Nidatech, "Fill–Master" (2 pages)– printout of Sep. 17, 1999.

* cited by examiner

Pin in Slot Robot

Robot in Channel

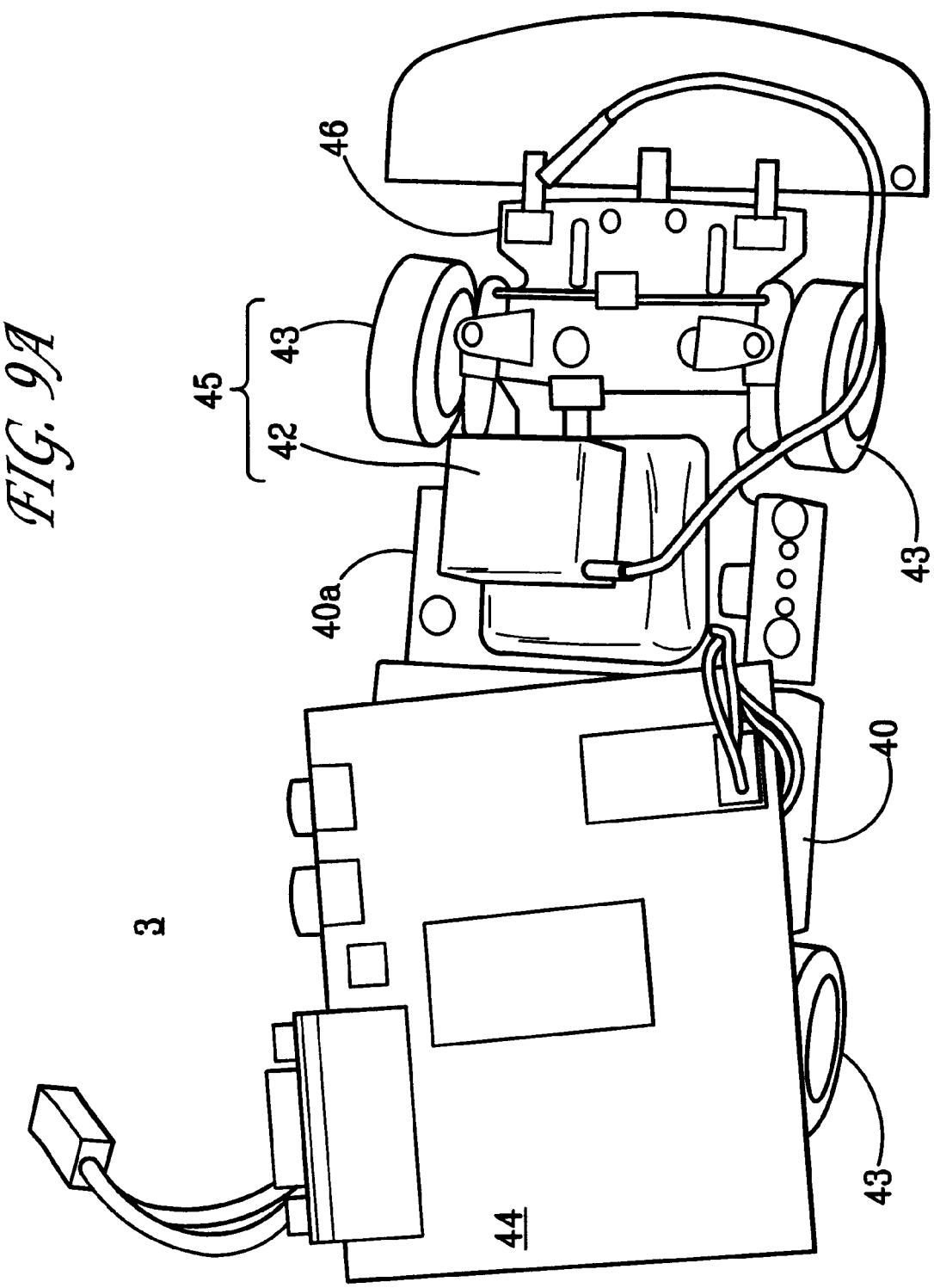

Robot Location Indexing at Destinations

Top View

Side View

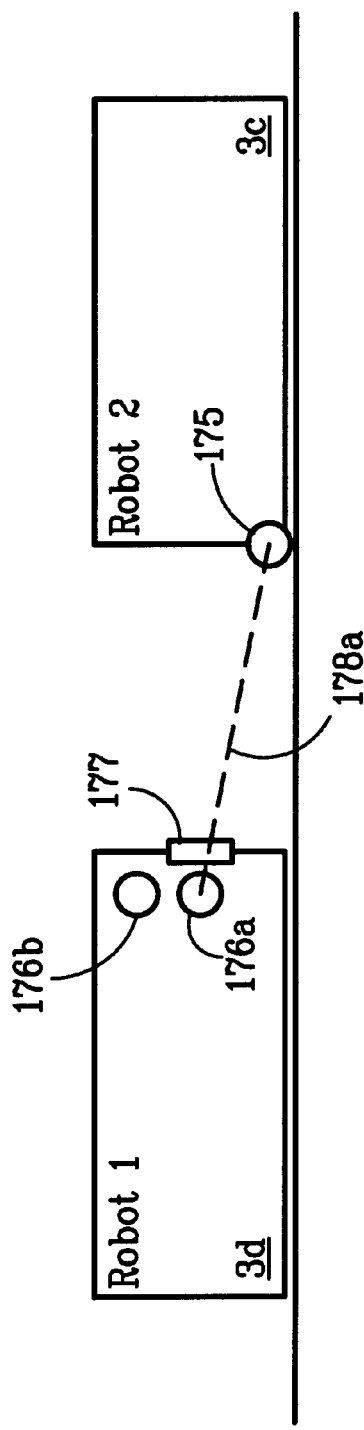
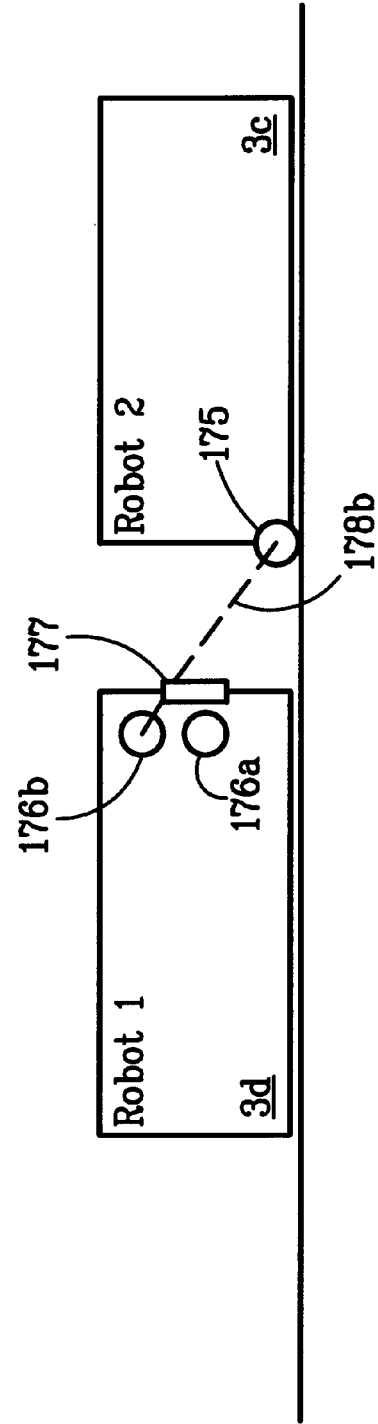
FIG. 17A
FIG. 17B

SYSTEM AND METHOD FOR SAMPLE POSITIONING IN A ROBOTIC SYSTEM

FIELD OF THE INVENTION

The present invention relates in general to automated systems for positioning a sample, or cargo. More particularly, the present invention relates to a robotic positioning system and method that include a gross positioning system for movement of the sample between workstations and a precision positioning system for precisely locating the sample at the workstation with respect to a device that will interact with the sample.

BACKGROUND OF THE INVENTION

Various industries require automated systems for the general movement of goods between workstations and a more precise positioning system for precisely locating the goods at each workstation for manipulation of the goods by a device at the workstation. For example, for pharmaceutical research and clinical diagnostics, there are several basic types of automation systems used. Each of these conventional approaches is essentially a variant on a method to move liquid or dry samples from one container to another, and to perform other operations on theses samples, such as optical measurements, washing, incubation, and filtration. Some of the most common automated liquid handling systems include systems such as those manufactured by Beckman, Tecan, and Hamilton.

These conventional automation systems share the characteristic that sample transfer and manipulation operations are carried out by workstations, or devices, of some kind. These workstations can be used separately for manual use, or alternatively, can be joined together in automated systems so the automation provider can avoid having to implement all possible workstation functions. Another shared characteristic is that samples are often manipulated on standardized "microtiter plates." These plates come in a variety of formats, but typically contain 96 "wells" in an 8 by 12 grid on 9 mm centers. Plates at even multiples or fractions of densities are also used.

In a first automation system, various workstations are linked together with one or more plate carrying robots. These robots can be a cylindrical or articulated arm robots, and can be located on a track to extend their range. A variant on this design is a system with one or more Cartesian robots operating over a work surface. In the Cartesian case, the robots can carry plates and also perform liquid transfer operations. These systems are controlled by a central control system with a scheduler. Most schedulers schedule the operations of one protocol performed many times, making sure that all time constraints are met, including, for example, incubation periods. The primary advantage of such a system is complete hands free operation. Accordingly, these systems can run for hours or days at a time with no human intervention. However, these types of systems have several disadvantages.

For example, individual devices can only be kept busy 30–70% of the time due to scheduling and collision avoidance constraints. In addition, the system has an upper limit on scalability. This second disadvantage comes about due to upper limits in achievable servo system dynamic range. All plate and liquid transfer operation require precision of about 0.1–0.5 mm. To do meaningful work, a work area of at least one square meter is typically needed. Servo systems that can achieve this dynamic range are expensive and relatively large. To increase the useable work area, dynamic range must be increased, without compromising the accuracy of the system. For these reasons, the largest linear dimension typically used is three meters. Smaller plates can increase the amount of work that can be accomplished in a given area, however, the necessary size of the high dynamic range servos prevents plates being used that are much smaller than the current standard.

A second basic type of automation can be created by using plate stackers. For example, an input stacker is placed on one side of a device such as a liquid transfer system or optical plate reader, and an output stacker is placed on the other. Plates are fed from the bottom of the input stacker to the device by conveyer belt or pick-and-place arm. When the device finishes an operation, the plate is similarly placed on the bottom of the output stacker. Stackers often use removable cartridges so that approximately 20 plates at a time can be carried from device to device. The cartridges are usually carried manually, however at least one system exists that uses an articulated arm robot to move the stackers between devices. Plate incubation is achieved by simply setting the stack in an incubator. The primary advantages of this automation approach are that the devices can be utilized nearly 100% of the time, and that it is relatively inexpensive to implement. However, this type of system has several disadvantages, including that the system is usually not fully automatic, that the plates cannot be processed with identical timing because the stacks are first in, last out, and that system flexibility is severely limited because stacks of plates must all be run through the same processing steps.

Another basic type of automation system is an extension of the above stacker type system wherein multiple devices are placed in a row on a lengthened conveyer. Although this system offers even more potential throughput, this type of system results in even less system flexibility. A further difficulty is that this type of system cannot accommodate incubation periods as there are no first in, first out stackers.

What is needed by various automation industries, such as the pharmaceutical discovery, clinical diagnostics, and manufacturing industries, is a sample positioning system and method that overcome the drawbacks in the prior art. Specifically, a system and method for providing a gross positioning system for moving samples between various stations coupled with a precision positioning system at each station for precisely locating the samples with respect to a device that will interact with the samples. Therefore, a need exists for an accurate sample positioning system and method that overcome the drawbacks of the prior art.

SUMMARY OF THE INVENTION

The present invention is directed to a system and method for positioning a sample, or cargo, with respect to a device in a robotic system. The system and method of the present invention provide both flexibility and scalability due to the benefit of queuing and the reduction in required dynamic range of the servos (e.g., actuators). The system and method of the present invention provide the flexibility of robots having autonomous navigation and stacker-like queuing for near 100% device utilization.

The system of the present invention includes a macro positioning system for "gross" movement of the sample between stations and a micro positioning system for precisely locating the sample at a station with respect to a device that will interact with the sample. The macro positioning system provides a positioning mechanism for the general movement of a sample along pathways formed between various destinations, or stations, wherein the sample is "grossly" positioned with respect to the station. Once at the station, the micro positioning subsystem disposed between a sample carrier, or robot, and the station provides a positioning mechanism for "precisely" positioning the sample in a predetermined location at the station with respect to a device that will interact with, or perform some function on, the sample. The system and method combine technologies for macro positioning between stations, micro positioning at each station, and device interaction with the sample at each station in a robotics system for accurately positioning a sample with respect to a device that will interact with the sample.

The macro position system preferably includes some type of track system disposed between and connecting the various stations, and thus defining the pathways. The track system of the present invention can comprise any standard track system, including for example, a grid-type, miniature railroad type, line follower-type, slot-follower, light or laser-follower, magnetic-follower. The track system defines one or more pathways and intersections connecting the various pathways which allow the robots to travel between the various stations.

The system includes one or more carriers, transporters, or robots that carry a sample, or cargo, around the pathways. Each robot includes a body, a track engagement mechanism, a sample holding device, a power supply, and a propulsion mechanism for propelling the robot along the pathways. Preferably, the robots of the present invention have an on-board controller which provides for autonomous navigation of the individual robots between the various stations in the system. Multiple robots running on a track system provides system flexibility and stacker-like queuing for near 100% device utilization. Autonomous navigation of the robots allows greater system flexibility because each robot individually controls its own navigation thereby reducing required dynamic range of the servos. The robots are programmed to negotiate the track system and travel to predetermined destinations within the robotic system, where they interact with a device. In addition, the system and robots provide for collision avoidance, error recovery, robot to station communications/identification, and provide more flexibility and stacker-like queuing for near full device utilization.

The micro positioning system of the present invention is preferably disposed between the robot and the stations and is used to precisely locate the robot, and thus the sample, in a predetermined location in space. The micro positioning system includes a locating fixture on one of the robot and the station and a cooperating location fixture on the other of the robot and the station. Preferably, the location fixture includes one or more projection extending from the robot and the cooperating location fixture includes one or more depressions formed at the station. The projections fit within the depression to form a self-centering and precision fit.

A further embodiment within the scope of the present invention is directed to a method of positioning a sample, or cargo, in a robotic system with respect to a device located at a station in the system. The method includes providing for the gross positioning or movement of a sample along pathways formed between various stations and also for the precision positioning of the sample in a predetermined location in space relative to a device at the station in order for the device to be able to interact with the sample. The method comprises providing a plurality of predetermined pathways connecting one or more stations, disposing one or more robots along the pathways, activating a macro position system, which is preferably located on-board the robot, to move the robots around the pathways, "grossly" positioning the robots with respect to a station, activating a micro positioning system, which is preferably disposed between the robot and the station, micro positioning the robot, and thus a sample on the robot, in a predetermined location in space with respect to a device at the station, and interacting with, or performing some function on, the sample with the device based on the identification.

Preferably, the method of the present invention also comprises using some type of track system between the stations thus defining the pathways and providing a mechanism for the robots to travel along. In addition, the method preferably further comprises establishing a communications link and identifying the robot to determine whether the robot is at a correct location. Furthermore, the method can further comprise recovering lost robots using an error recovery system and avoiding collisions between robots using a collision avoidance system.

The system and method of the present invention provide for improved scalability both toward large and small systems, unlimited flexibility, allowing any sample to be processed following any protocol, stacker-like queuing for near 100% device utilization, and completely hands free operation.

BRIEF DESCRIPTION OF THE DRAWINGS

The foregoing and other aspects of the present invention will become apparent from the following detailed description of the invention when considered in conjunction with the accompanying drawings. For the purpose of illustrating the invention, there is shown in the drawings an embodiment that is presently preferred, it being understood, however, that the invention is not limited to the specific methods and instrumentalities disclosed. In the drawings:

FIG. 9A is a top view of another exemplary robot of the system of FIG. 1 with the sample holding device removed for clarity;

FIGS. 17A and 17B are schematic diagrams showing an exemplary rear-end collision avoidance system in accordance with the present invention;

DETAILED DESCRIPTION OF PREFERRED EMBODIMENTS

The present invention is directed to a highly accurate system and method for the movement and positioning of a sample in a robotic system. The system and method of positioning the sample, or cargo, within the robotic system use a gross positioning subsystem (hereinafter also referred to as "macro positioning system") in combination with a precision positioning subsystem (hereinafter also referred to as "micro positioning system"). The macro positioning system provides a positioning mechanism for the general movement of a sample along a pathway between various destinations, or stations, wherein the sample is "grossly" positioned with respect to the station. Once at the station, the micro positioning system provides a positioning mechanism for "precisely" positioning the sample in a predetermined location at the station with respect to a device that will interact with, or perform some function on, the sample.

The subject invention combines technologies for macro positioning between stations, micro positioning at each station, and device interaction with the sample at each station in a robotics system for accurately positioning a sample to be worked on with respect to a device that will perform the work. This provides for near unlimited range of the system with very precise final positioning at each destination at relatively low cost. Preferably, the micro positioning system positions the sample with respect to the device to a magnitude in the order of about 10× or better than the macro positioning system.

Furthermore, the present invention can provide for autonomous navigation wherein the robots make all navigational decisions, including turning, speed, collision avoidance, and error recovery. System flexibility and scalability result in part as a by-product of being able to afford many sample moving robots, hence they can sit around waiting in line for a device to be free (thus providing stacker-like queuing for near full device utilization).

Figure 1:
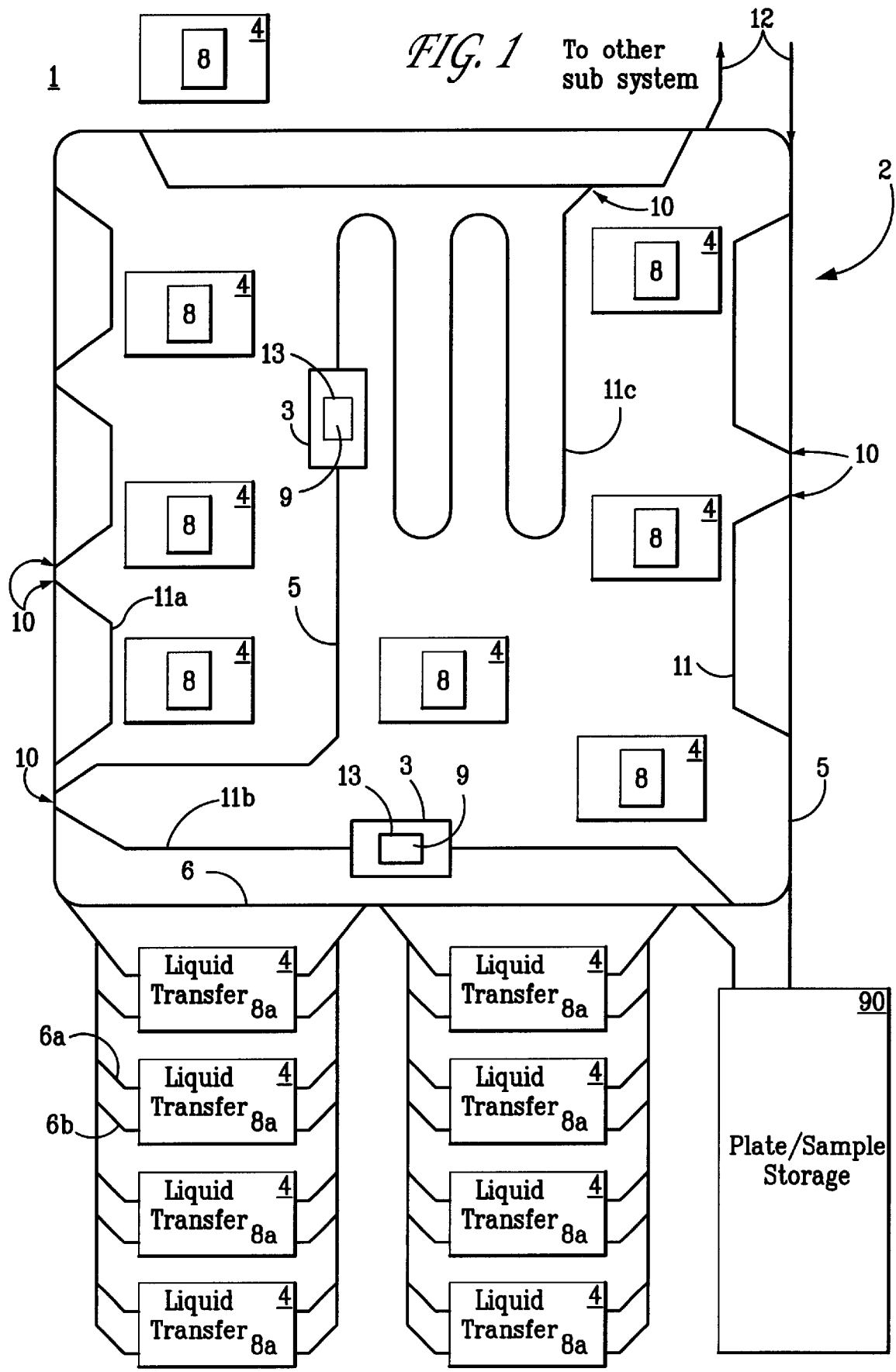
FIG. 1 is a schematic diagram of an exemplary layout of the positioning system in accordance with the present invention.

FIGS. 1, 3, 4, 5A, and 5B illustrate several exemplary embodiments of the macro positioning system 2, which provides for the gross movement of one or more sample carriers 3 (hereinafter also referred to as "transporters" or "robots"), between one or more destinations 4 (hereinafter also referred to as "stations" or "workstations"). As shown in FIG. 1, the present invention has predetermined pathways 5 defined between the one or more stations 4 in the system 1. As shown in FIGS. 1, 3, 4, and 5, each of the following embodiments preferably has some kind of track system 6 disposed between the various stations 4 that one or more robots 3 travel along and follow.

The present invention is not limited to a macro positioning system 2 having a track system 6. For example, the robots 3 could be constructed to navigate the pathways 5 guided by any standard navigational means, including fixed beacons disposed about the desired pathway of a given application, a G.P.S., etc.

As shown in FIG. 1, the track system 6 defines one or more predetermined pathways 5 disposed between the various stations 4. Each station has a device 8, such as a plate washer, pipettes, a reader, etc., for interacting in some way with the robot 3 and/or a sample 9 thereon. Intersections 10 are formed along the various pathways 5 where the pathways diverge and converge, and where devices are located. One or more siding 11 can be provided at each station 4 for allowing a robot 3 to exit a pathway 5 onto the siding 11. The siding 11 for a device 8 allows other robot 3 traffic to pass while the robot 3 and device 8 interact. As shown in FIG. 1, each siding 11 may comprise a relatively short siding 11a, a longer siding 11b allowing a queue of robots to wait for a slow device, or a relatively very long siding 11c which can hold a very long queue for slower devices. An indicator device (not shown) can be provided at each intersection 10 and at each station 4 which can be detected by a sensor device (not shown) on each robot, for determining when a robot 3 is at an intersection 10 or station 4.

Figure 2A:
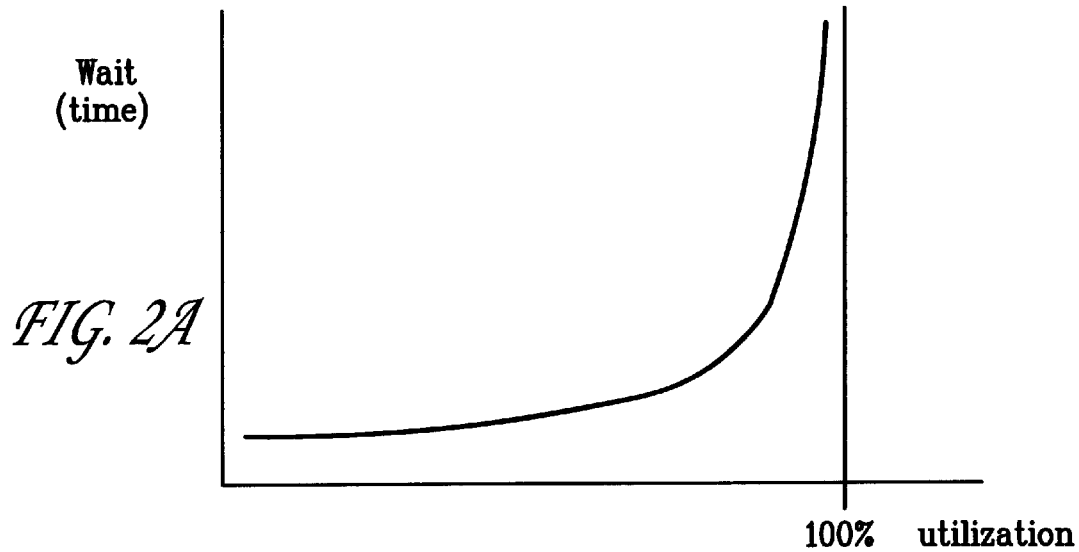
FIGS. 2A, 2B, 2C are graphical representations of an exemplary queuing system in accordance with the present invention.
Figure 2B:
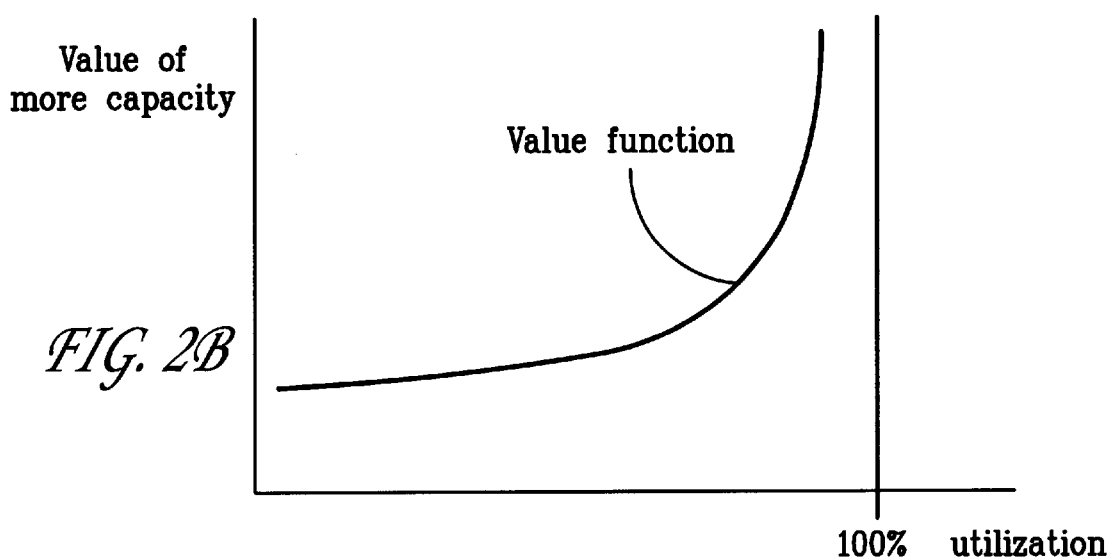
Figure 2C:
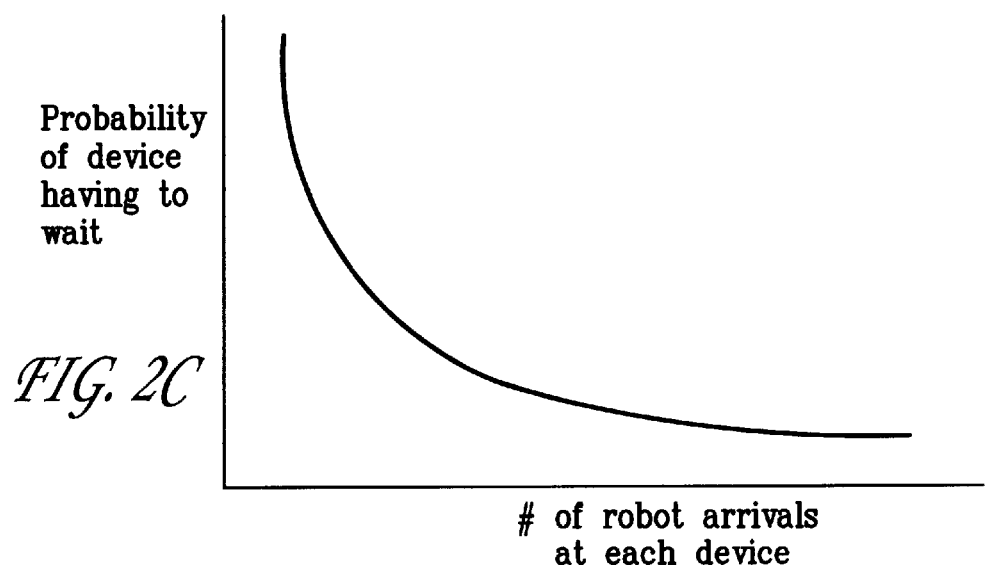

As shown in FIG. 2A through 2C, the robotic system can be viewed as a queuing system, where queue congestion grows asymptotically as device demand approaches robot capacity, as shown in FIG. 2A. The value of capacity (e.g., the number of robots) grows with increased congestion resulting form devices having to wait for another robot, as shown in FIG. 2B. A standard queue function, such as in an M/M/S queue, can be used to represent the probability of a device having to wait and to approximate the value of more robot carrying devices as a function of congestion, as shown in FIG. 2C. The system and method of the present invention address this problem by providing the flexibility of multiple robots traveling on a track system thereby providing stacker-like queuing for near 100% device utilization, as well as robots having autonomous navigation.

The system 1 can include a cross-connection pathway 12 for coupling the main system 1 to one or more subsystems (not shown). The cross-connection pathway 12 can connect the main system 1 to a subsystem that is a few meters away, or even in another building that may be hundreds of meters or kilometers away. Alternatively, the cross-connection pathway 12 can also connection one or more subsystems positioned above or below the main system 1, such as, for example in a stackable type arrangement.

The system 1 includes a sample, or cargo, holding device 13, such as a plate or matrices, for holding the sample 9 on the robot. As shown in FIG. 1, for example, liquid transfer devices 8a move liquid from a sample plate 13 on one robot to another. This can be accomplished by sending the two robots 3 to the two appropriate parallel tracks 6a, 6b which travel under the same device 8, such as a pipette or pin transfer device.

The system 1 layout described above with respect to FIG. 1 is two dimensional (e.g., the system is contained within a plane defined by the X, Y coordinates). Alternatively, the system 1 could be built on multiple levels, or in three dimensions for even more operations per cubic meter of lab space (e.g., the system could be contained within a space defined by the X, Y, and Z coordinates).

The topology of all the embodiments shown in FIGS. 1, 3, 4, and 5 is preferably designed such that every intersection 10 has a fork design, with only left and right choices. Accordingly, as shown, a single pathway 5 splits into two pathways (e.g., diverges). The track system 6 is preferably arranged such that travel on any given section or pathway 5 is generally only in one direction, like for example, an automobile freeway system. Accordingly, to return to the same position, a robot 3 would make a complete circuit around one of the loops in the system 1. Preferably, the topology is further limited so that only two pathways 5 ever come together (e.g., converge into one path) at once.

The system can also provide for reverse direction of the robots (e.g., backing up). Preferably, this reverse direction capability is provided at at least the local regions where the robots are precisely positioned. For the grid-type track system, as described more fully herein below with reference to FIG. 3, this is relatively easy to implement by, for example, having the on-board controller simply change the "back" to the "front" and reversing the direction of rotation of the wheels. For the slot and channel type track systems, this can be accomplished, for example, by disposing a pair of side rails along side the main pathway, or a rear-end guide pin, to prevent the robot from jack-knifing as it attempts to reverse directions.

Figure 3:
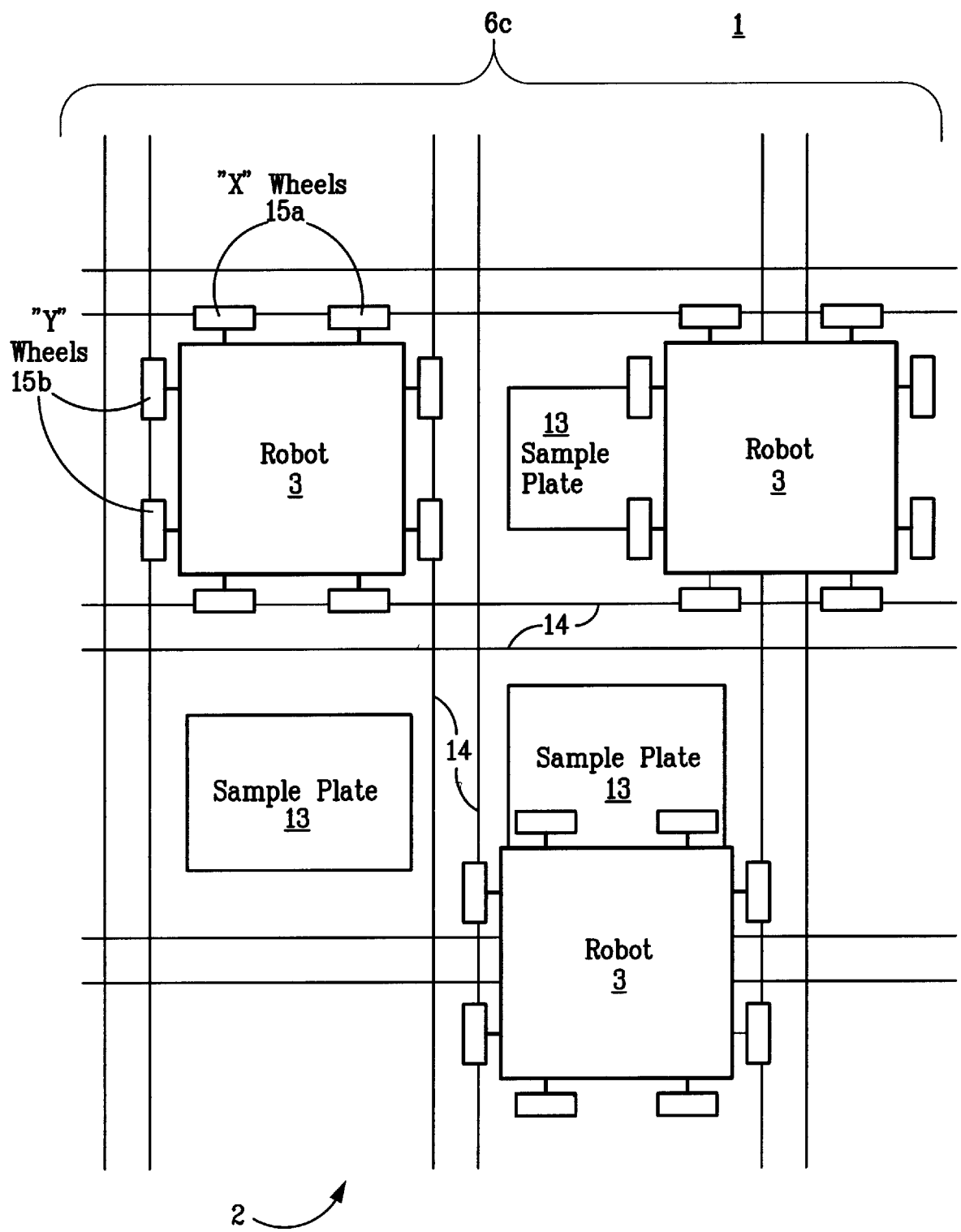
FIG. 3 is a schematic diagram of an exemplary grid type track system for movement of the robots between stations in accordance with the present invention.

FIG. 3 shows a grid-type, or array-type, track system 6c which is designed to create an arbitrarily large work surface on which robots 3 carrying plates 13 having a sample 9 are set to be moved between workstations 4 having devices 8 which interact in some way with the sample 9. Plates 13 are moved from one location 4 to another location 4, and to devices 8 and bulk storage 90, by robots 3 which can travel in X or Y directions along the grid system 6c. Interaction between the cargo 9 (e.g., cargo manipulation), such as, for example, liquid or dry sample handling, can be accomplished by devices 8 at each station 4 or similar robots 3 which carry devices 8, such as pipettes or pin transfer tools. Because these robots 3 are inexpensive, a variety of pipette and pin sizes can be accommodated by multiple dedicated robots.

FIG. 3 shows the basic layout of these robots 3 on the grid 6c. Rails 14 are provided upon which the robots 3 run. As shown, each robot has a set of "X" wheels 15a and a set of "Y" wheels 15b. If the robot 3 is centered on a grid location and either changing direction or interacting with a plate, both sets of wheels are raised and the robot rests on its micro positioning subsystem 60, such as, for example, indexing feet, as described herein below in more detailed with respect to FIGS. 11A and 11B. If the robot 3 wants to move on the "X" direction, it lowers its "X" wheels 15a and rolls in that direction. If it wants to change to travel in the "Y" direction, it raises the "X" wheels 15a while at an intersection 10 (plate grid location), then lowers the "Y" wheels 15b. Note that this also realigns the robot ensuring that the new wheel set will properly engage.

In another embodiment of the track system (not shown), the robots can run on miniature railroad tracks, such as, for example, model train tracks. Intersections can be detected by a mechanical, electrical, or IR sensor. The intersections can be switched either by conventional moving switches, or by open switches, such as those used by trolleys. In the first case, the switches are either thrown by a mechanical arm on the robot as it approaches, or by a signal (e.g., an IR or an electrical signal) to a track mounted switch actuator. In the second case, a turning force is applied to the wheels as they pass over a switch causing the wheels to turn thereby causing the robot to go one way or the other.

In another embodiment (not shown), the track system can comprise a line follower-type track system. In this embodiment, the robots follow lines of contrasting color to the work surface in the infrared. This can be accomplished, for example, using three reflective sensors. The computer steers left or right depending on which sensors detect the line. When an intersection is detected, the robot steers through it by ignoring the sensor on the side it does not want to go. This causes the robot to follow the edge of the line in the direction it wants to go. It does this for a predetermined distance and then it resumes normal line tracking. Preferably, this embodiment includes a power supply on-board the robot to power the robot, such as rechargeable batteries. A robot having an on-board power supply can return to a charging station periodically for recharge or battery swap.

In another embodiment of the track system, the track system comprises a slot or channel follower-type track system. In these embodiments, the robots follow a slot with a pin, similar to a slot car, or run in a channel as wide as the robot.

Figure 4:
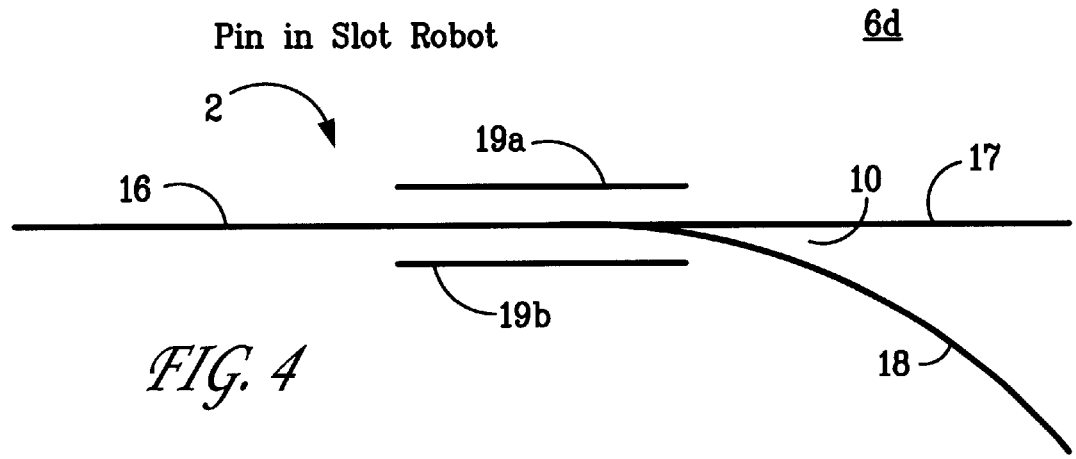
FIG. 4 is a schematic diagram of an intersection of an exemplary slot follower type track system for movement of the robots between stations in accordance with the present invention.
Figure 5A:
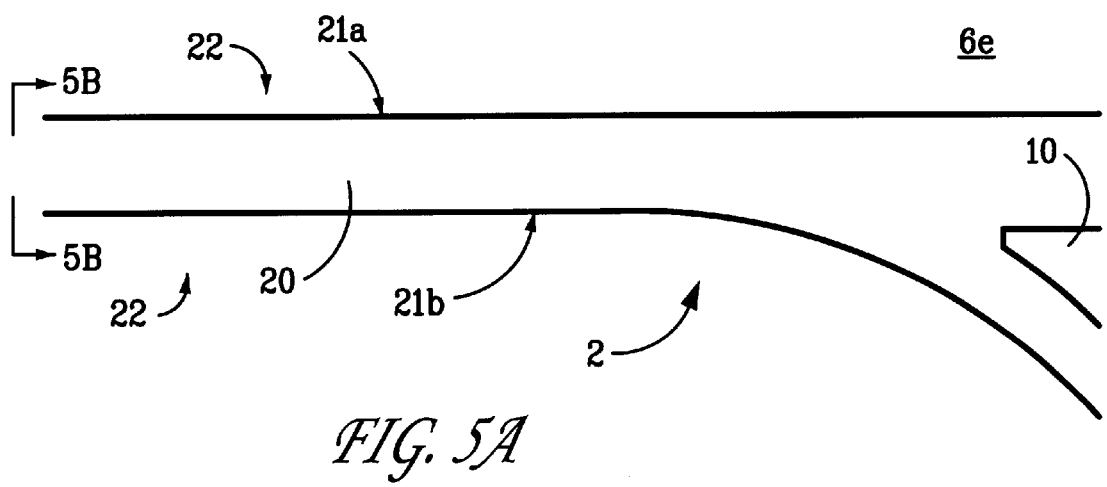
FIG. 5A is a plan view of an intersection for an exemplary channel type track system for movement of the robots between stations in accordance with the present invention.
Figure 5B:
FIG. 5B is a cross-sectional view of the channel type track system of FIG. 5A taken along line 5B—5B.

FIGS. 4, 5A, and 5B show methods for negotiating an intersection 10 for two types of track systems 6. As shown in FIG. 4, guide slots 19a and 19b can be provided in addition to the main slot 16, which forks into left slot 17, and right slot 18. Upon detection of an intersection 10, an auxiliary pin (not shown) can be lowered from the robot on either the left or right side of the robot body, depending on the direction desired. This pin forces the robot to follow the desired path through the intersection 10. Optionally, the pin in the main slot 16 may be removed or lifted during travel through the intersection to allow for tolerances in following the auxiliary slot 19a or 19b. In a second alternative embodiment (not shown), wherein the robot follows a slot type track system 6d, with a pin, another method of choosing a direction is by causing the wheels of the car to turn, pushing the pin to the side of the slot desired to turn.

FIGS. 5A and 5B show a channel type track system 6e. As shown in FIG. 5B, where the robot (not shown) runs in a channel 20 as wide as its body width, the top of the channel walls 21 is preferably at least partially above the work surface level 22. To choose a direction at an intersection 10, an arm (not shown) connected to the robot body can be lowered which hooks over a left 21*a* or right wall 21*b* to force the robot to hug the side wall 21 in the direction of choice.

Figure 6:
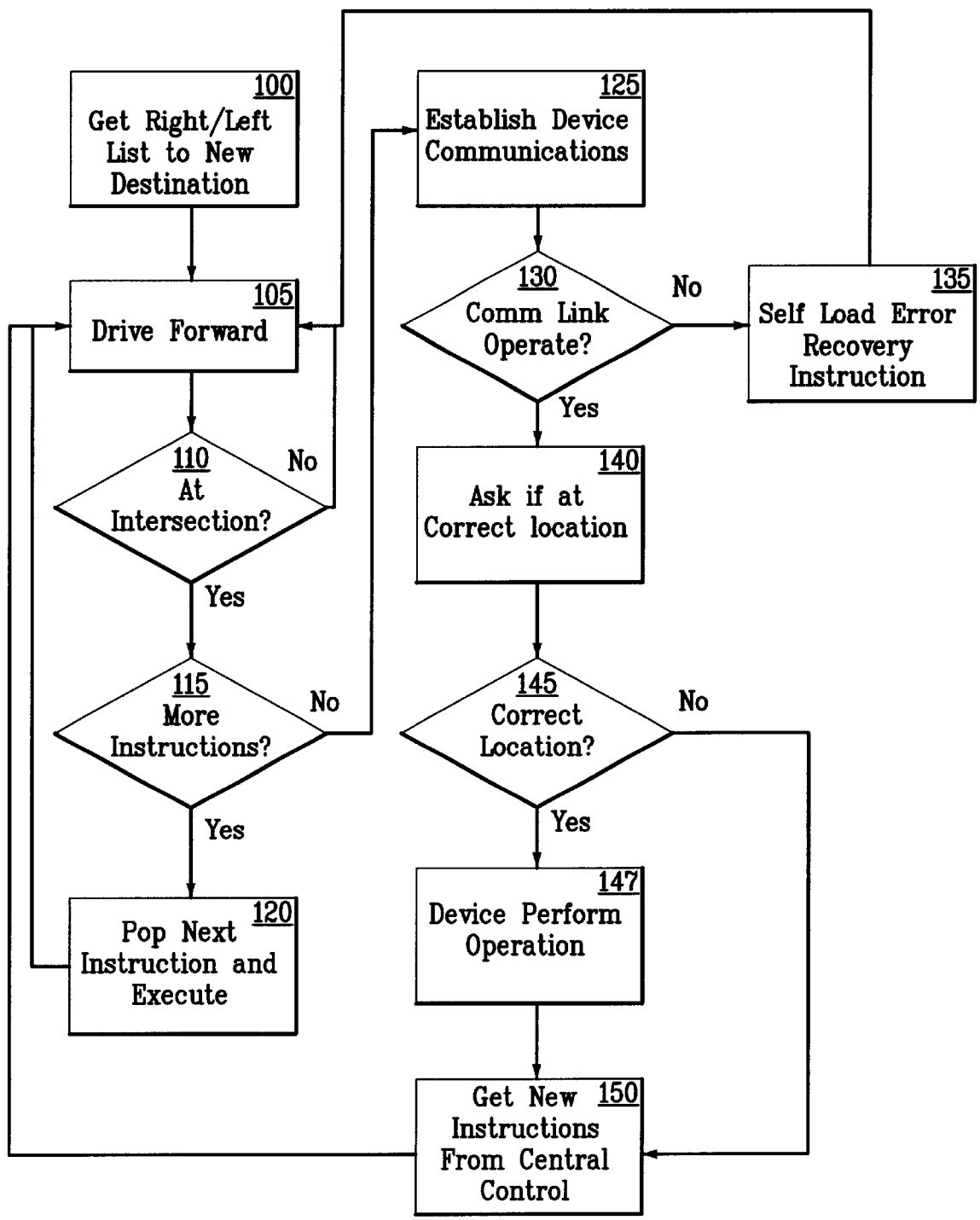
FIG. 6 is a flow chart of an exemplary method of navigation in accordance with the present invention.

FIG. 6 is a flowchart showing an exemplary method for navigation in accordance with the present invention. As shown in FIG. 6, the robot gets instructions, such as, for example, a left/right list, to the new destination, or station, at step 100. The propulsion system is activated causing the robot to drive, or move, forward, at step 105. The robot continues along the pathway as long as it does not sense an intersection. When the robot senses that it has come to an intersection, at step 110, it then determines whether there are more navigation instructions, at step 115. If there are more instructions the robot inserts/executes the next set of instructions, at step 120, and then continues to drive forward, back at step 105. The process of steps 100 through 120 are repeated until it is determined that there are no more instructions, at step 115. When the end of the list is reached, the next intersection is assumed to be the destination, where the robot stops and attempts to communicate with the device it is at.

Once no more instructions are detected, or a station is detected, at step 115, the robot attempts to establish communications with a device, at step 125. The robot determines, at step 130, whether or not a communications link is established. If no communications link is established, then the robot activates an error correction, such as, for example, initiating a preprogramed error recovery instruction, at step 135, and drives forward, at step 105.

If a communications link is established and operating at step 130, then the robot identifies itself to the device, at step 140. At step 145, it is determined whether the robot is at the correct location. If the robot is not at the correct location, the robot gets new instructions from a central controller, at step 150, and then drives forward, at step 105.

If it is determined that the robot is at the correct location, at step 145, then the device interacts with the robot and/or sample on the robot, such as for example performing one or more operations and/or manipulates a sample on the robot, at step 147. After the device has completed its interaction with the robot, the robot gets new instructions, at step 150. The process then continues, at step 105, and the robot drives forward.

Preferably the robot is capable of autonomous navigation. Autonomous means that the controller that controls the movement of the robot along the pathways as it travels around the system is located on-board the robot. For example, the robot makes all the navigational decisions, including when to turn, where to turn, what route to take, what speed to travel at, when to stop, etc. In addition, the navigational system provides for error correction and collision avoidance, which are also preferably controlled on-board the robot. Autonomous navigation of the robot provides system flexibility and reduces system costs. Alternatively, the controller for controlling the movement of the robot can be located in other locations within the system, such as in the stations or devices, as part of the central controller, etc. An intersection can be detected by, for example, an optical, electrical, or mechanical switch.

Figure 7:
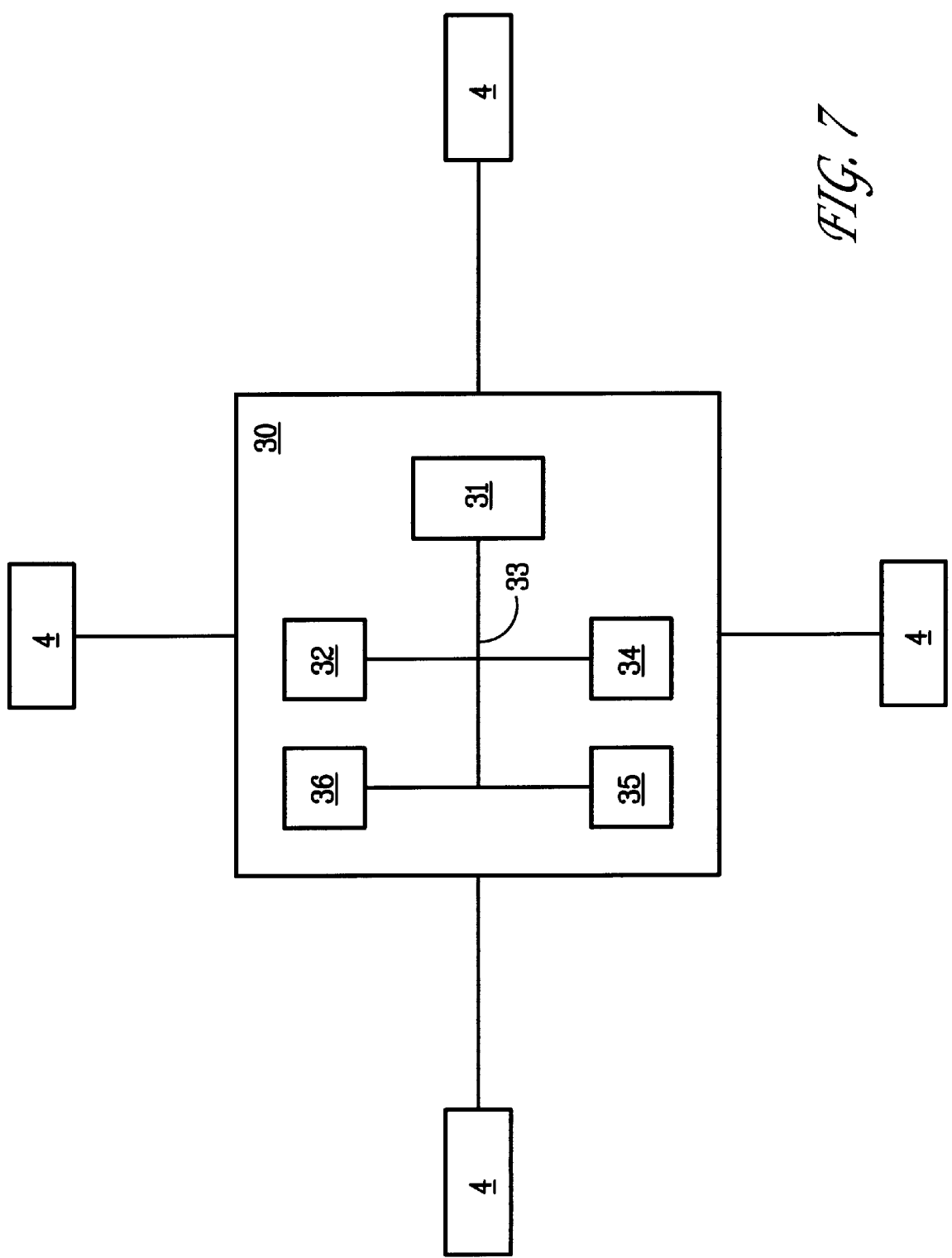
FIG. 7 is a block diagram of an exemplary central controller connected to the stations in accordance with the present invention.
Figure 8A:
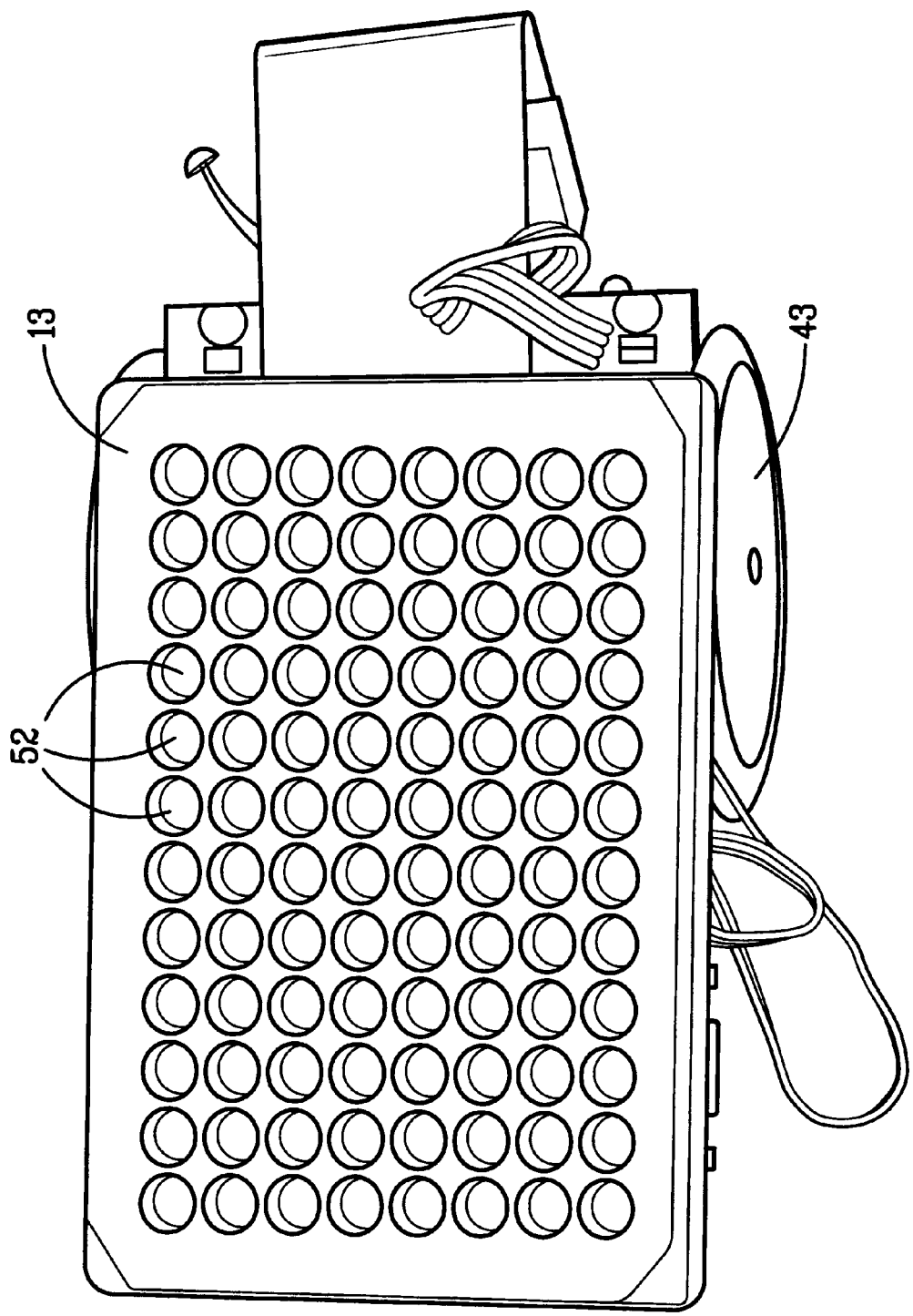
FIG. 8A is a top view of an exemplary robot of the system of FIG. 1.
Figure 8B:
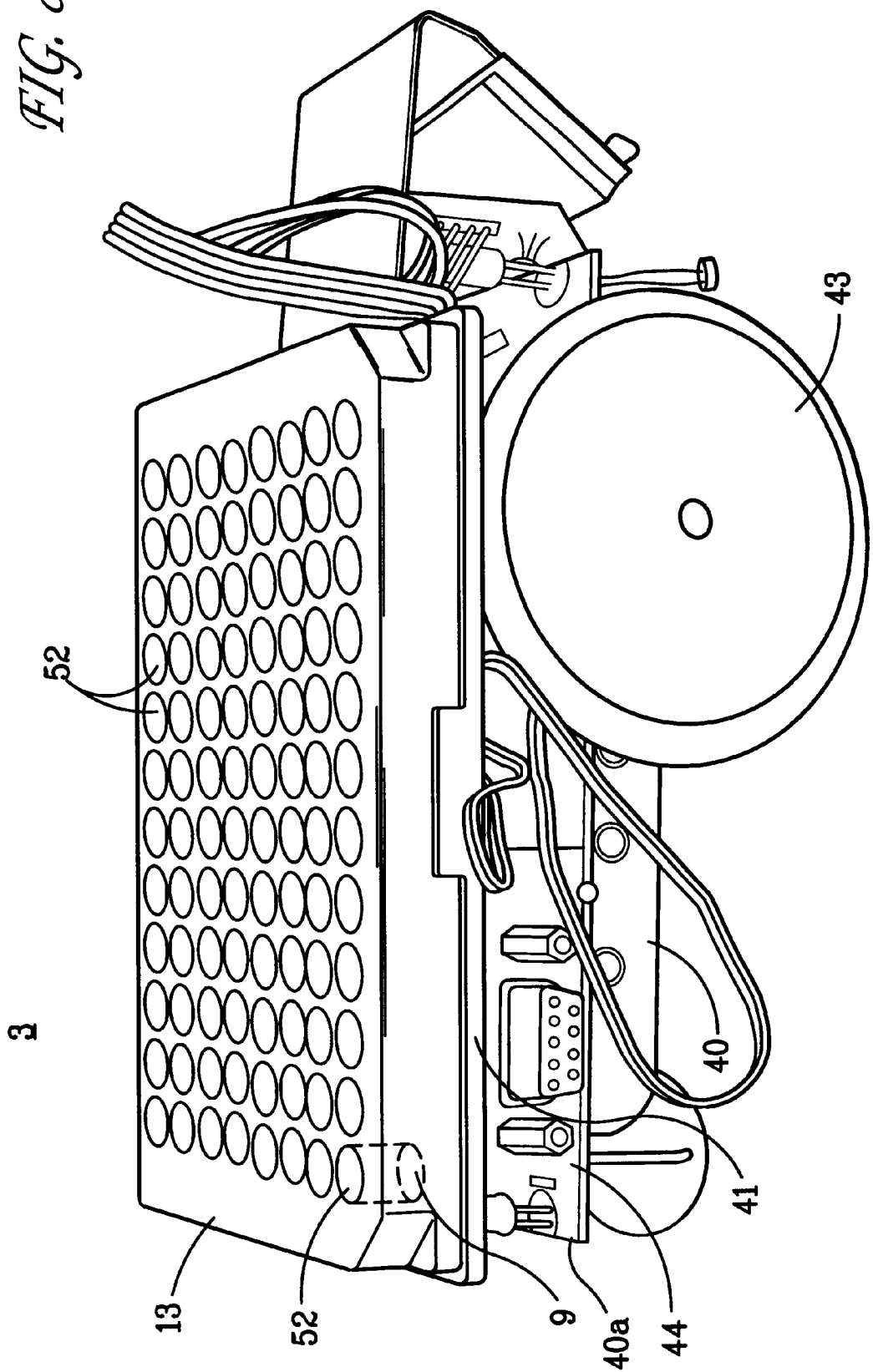
FIG. 8B is a side view of the exemplary robot of FIG. 8A.
Figure 8C:
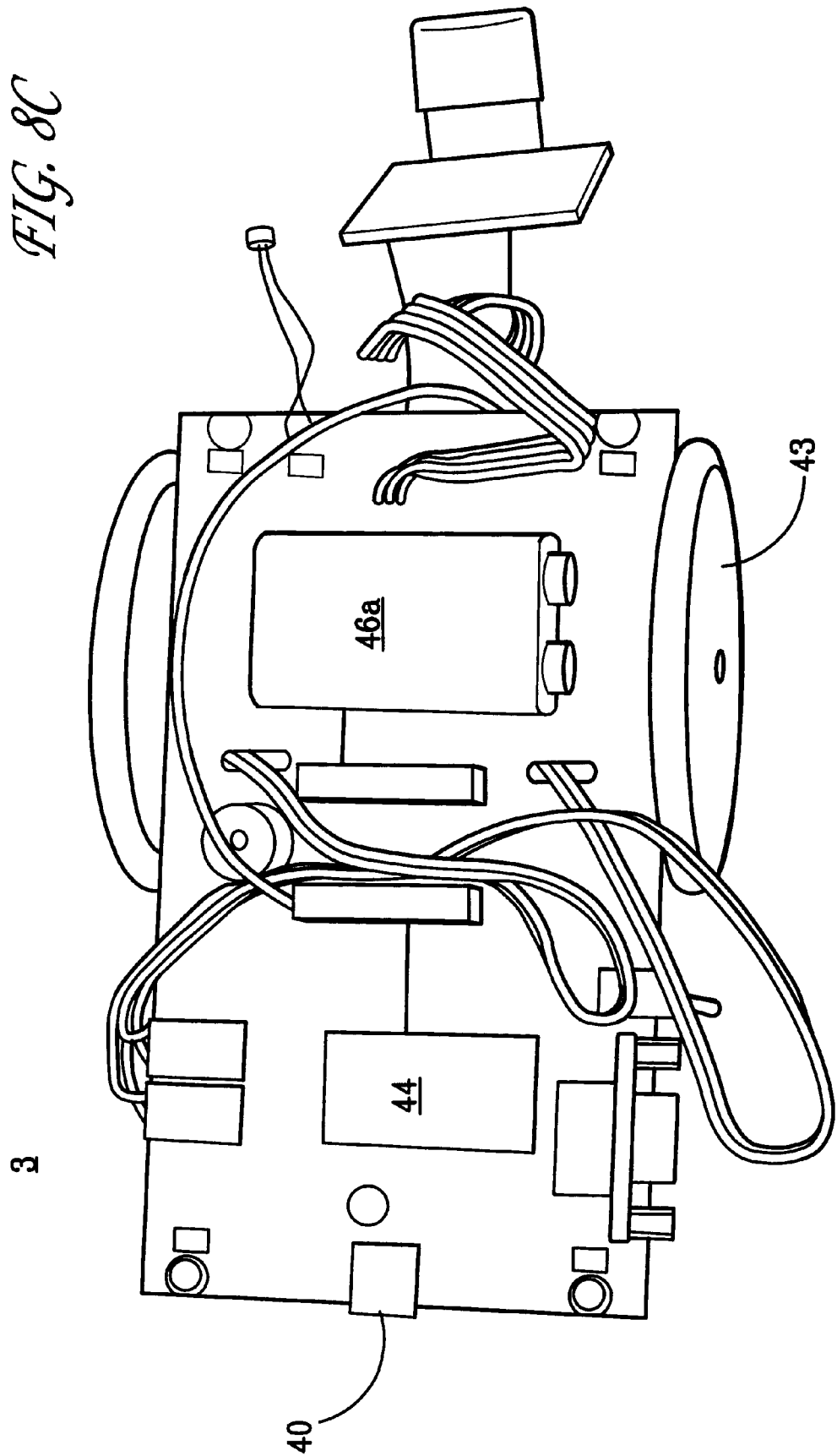
FIG. 8C is a top view of the exemplary robot of FIG. 8A with the sample holding device removed for clarity.

FIG. 7 is a schematic diagram of an exemplary central controller 30 in accordance with the present invention. As shown, each station 4 is coupled to the central controller 30 having a microprocessor 31. The microprocessor 31 preferably generates the routing information and can perform tracking and other processing functions. Each station 4 can be connected to and communicate with the central controller 30 using standard wired or wireless techniques. This allows the central controller 30 to send navigational instructions to each robot 3 via a communications link or interface between the station 4 and the robot 3. The robots can follow one or more protocols as defined by the central controller 30.

As shown, the microprocessor 31 can reside in a conventional computer, such as a standard personal computer, which can comprise the central controller 30 (e.g., 100 MHZ, 32 Mbyte DRAM, monitor, keyboard, ports, hard drive, floppy drive, CD-ROM drive). Alternatively, a microprocessor can reside within each station 4.

The microprocessor 31 is coupled to each station 4 via conventional cables and/or printed circuit boards (PCBs) that can be connected into slots on the computer, such as an ISA slot or a PCI slot. Other conventional means for coupling the stations to the microprocessor 31 can be employed, such as, for example, a standard Ethernet, USB, or wireless connection.

The microprocessor 31 preferably provides navigational instructions to the robots for the movement of the robots, schedules the operation of the devices, and runs software held in read only memory (ROM) 32. The processor 31 is connected via a bus 33 to the ROM 32, a random access memory (RAM) 34, another memory such as an erasable programmable ROM (EPROM) 35, and an input/output (I/O) controller 36. The RAM 34 is large enough to hold at multiple protocols, robot and sample identification data, and navigational instructions for each robot. The I/O controller 36 is connected to the appropriate circuitry and drivers (not shown) for issuing commands and instructions to the stations 4.

FIGS. 8A, 8B, 8C, 9A, 9B, and 9C show two exemplary robot 3 embodiments in accordance with the present invention. As shown, the robot 3 includes a body 40, a sample holding device 13, a portion of the micro positioning system (see FIGS. 11A, 11B, and 12), a propulsion mechanism 42, and track engagement mechanism 43. Preferably, the body 40 includes a sub-frame 40*a*. Each robot 3 also includes a controller 44, a drive system 45, and a power supply 46. The robot can include various displays (not shown) and/or indicators (not shown) for showing a state of the robot 3. Preferably, the robots 3 has an on-board controller 44, an on-board drive system 45, and an on-board backup power supply 46. For example, the on-board drive system 45 can be a motor and gear system, and the on-board backup power supply 46 can be a battery or a capacitor. In addition, the robot 3 can include an identification system, a collision avoidance system, and an error correction system.

The sample, or cargo, holding device 13 is used for hold one or more samples 9, or individual pieces of a cargo, on the robot 3 for interaction with one or more of the devices 8. The sample holding device 13 is preferably attached to or placed on top 41 of the robot body 40, such as on top of the sub-frame 40*a*. For example, an exemplary sample holding device for a typical liquid-type handing system, as shown in FIG. 1 and in more detail in FIGS. 7A and 7B, comprises a plate 13 having one or more wells 52, or cavities, formed therein.

The plate 13 can be, for example, any standard microtiter plate format, such as a 96-well plate, a 384-well plate, a 1536 well plate, etc. The wells 52 may be varying depths, such as shallow or deep well. The wells 52 may have a variety of shapes based on the application and the samples that they will carry and the wells can have a flat, a U-shaped, or a V-shaped bottom. Preferably, the well plates 13 meet SBS standards, are made from optically quality polystyrene to allow direct sample observation, and have raised rims (not shown) to prevent cross-contamination. Alternatively, the sample holding device 13 can include any other size or type of container or platform depending on the particular application, such as standard or non-standard sizes of, for example, a vial, a test tube, a pallet, a cup, a beaker, a matrices, etc.

This robotic sample positioning system 1 is conceived to be implemented in multiple scales. For example, in a first embodiment of the invention, the scale can be designed to work with standard size microtiter plates. These standard plates are approximately 125 mm by 85 mm. The wells of a 96-well plate are on about 9 mm centers and hold from about 200 $\mu$l to about 1500 $\mu$l depending on the plate depth. This system could work with standard devices currently available, such as, for example, plate washers, pipettes, plate readers, etc. In another embodiment of the invention, the scale could be significantly smaller. For example, a 96-well plate could be approximately 16 mm by 12 mm, with wells on about 1 mm centers. These wells would hold approximately 1 $\mu$l. Liquid could be transferred by a device, such as a micro-pin tool or a piezo-pipette.

Figure 9B:
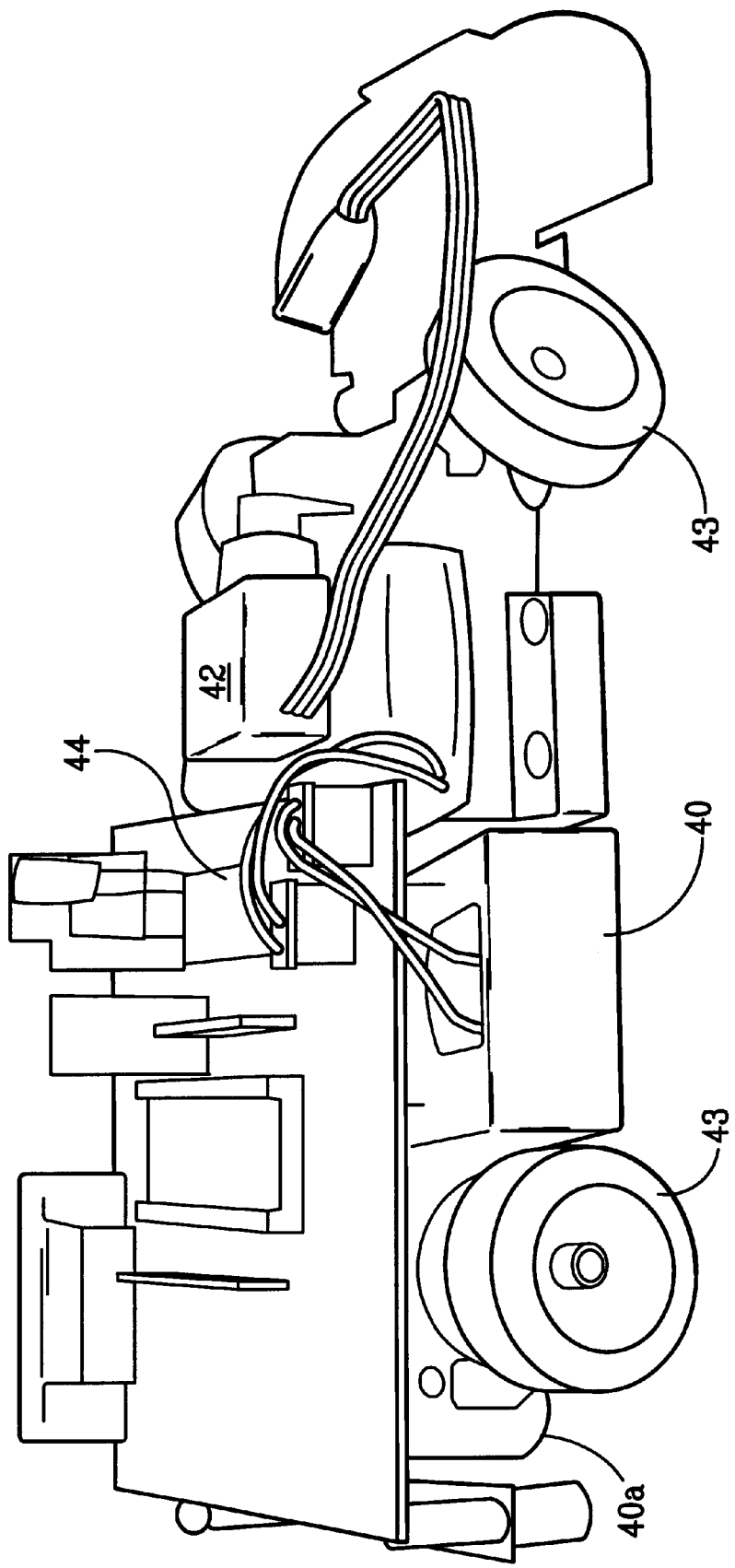
FIG. 9B is a side view of the exemplary robot of FIG. 9A.
Figure 9C:
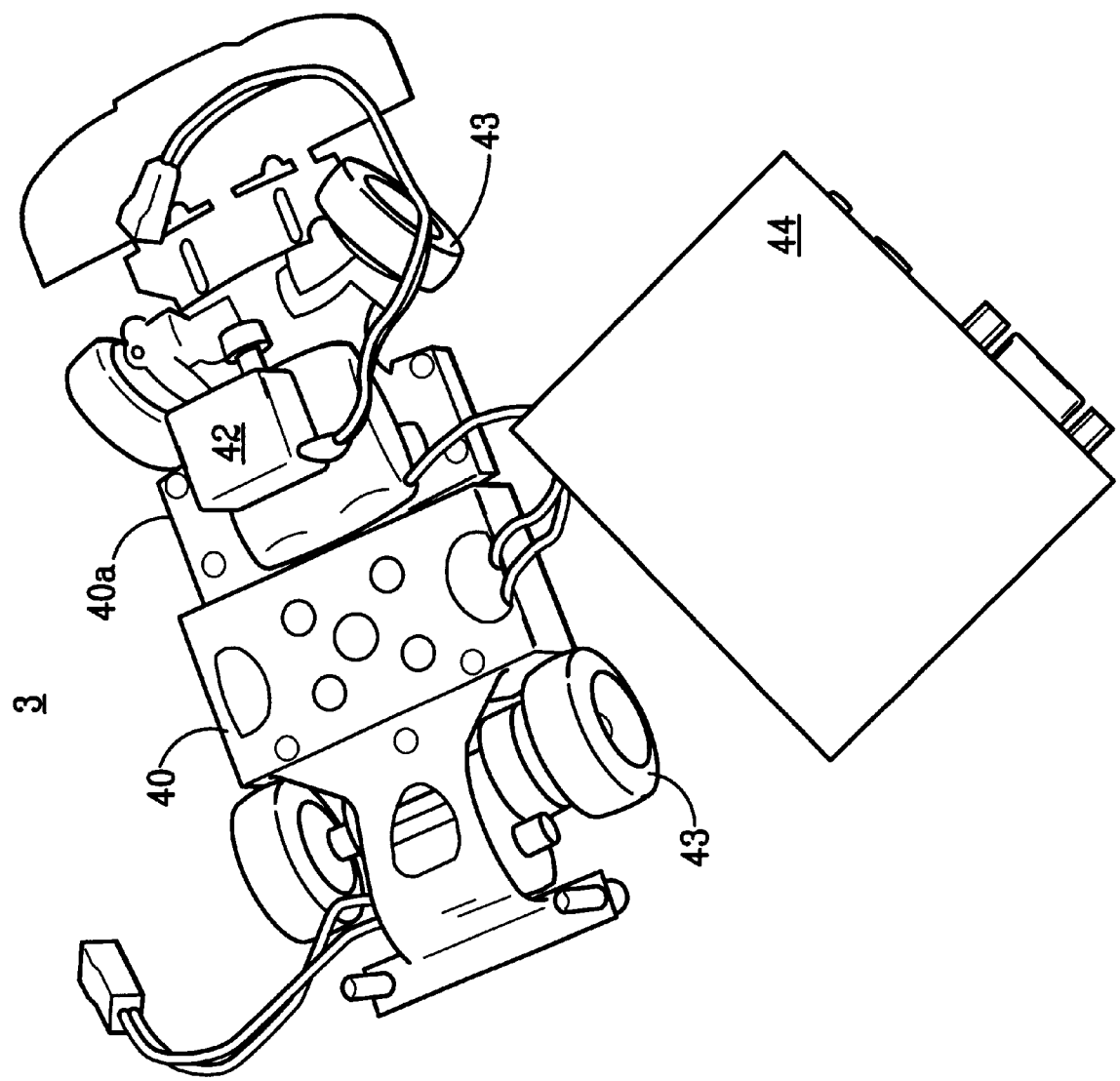
FIG. 9C is a top view of the exemplary robot of FIG. 9A with the controller removed for clarity.

The robot 3 includes a propulsion system 42 for propelling the robot 3 about the system 1 along the various pathways 5. Any known technique for propelling a device can be used to propel the robot 3 around the pathways 5 of the system 1. For example, exemplary robot propulsion systems 42 can include an electric propulsion system, such as an electric motor, a pneumatic propulsion system, such as a fan or air powered firing pins, a magnetic propulsion system, etc. Preferably, the robot propulsion system 42 is located on-board the robot 3, as shown in FIGS. 9A and 9B. Motion control can include technologies, such as PWM servos, motors with once per revolution encoders from rough speed regulation and Nitinol thermally activated memory metals. The motion controller can include a Motor Mind B and Mini SSCII (Serial Servo Controller) manufactured by Solutions Cubed of Chico, Calif. Alternatively, the propulsion system can be located along the pathway such that it engages and propels the robot along the pathway.

The robot 3 includes a power supply 46, which can comprise a standard DC or AC supply, a battery, or a capacitor (not shown). Preferably, during normal operating conditions the robot 3 is powered via a standard DC or AC supply and has an on-board power supply 46a for those periods of time wherein the normal power supply may be temporarily interrupted or lost, as for example, when the robot 3 is making turns or experiences a dirty stretch of track 6. The on-board power supply 46a preferably has sufficient power to allow the robot to travel at least about 10 cm. The robots 3 can derive power from the track 6 that they ride upon.

The track engagement mechanism 43 is attached to the body 40 and can include, for example, wheels, rollers, sliders, slots, pins, etc. The track engagement mechanism 43 is used for engaging the track system 6 thereby holding the robot 3 on the track system 6 and also for engaging the track system 6 thereby allowing the robot 3 to move forward around the various pathways 5.

Figure 10:
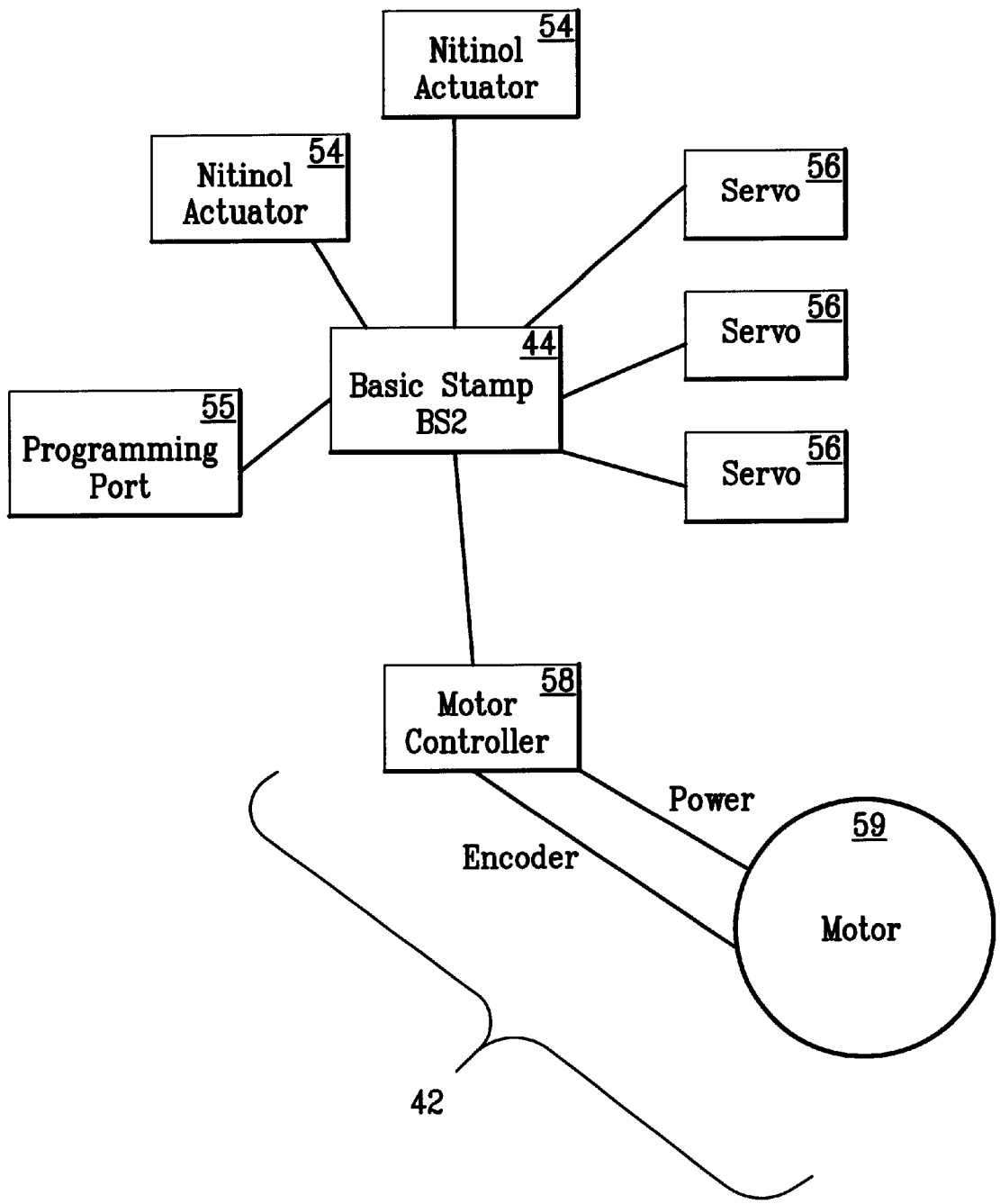
FIG. 10 is a block diagram of an exemplary robot controller to be used with a robot of FIGS. 8 and FIGS. 9.

FIG. 10 is a block diagram showing an exemplary controller 44. Preferably, the robots 3 have on-board control computers. The on-board computers are used to control and operate the robot, including the autonomous navigation of the robot. Preferably, the on-board computer includes a programming port 55 with the ability to load programs remotely, a non-volatile RAM for both the program loaded itself, with room for some program accessible RAM, an I/O control pins which can drive PWM servos 56 (such as, for example, remote control model airplane servos), perform bi-directional serial communication, and one or more actuators 54. Also, the robot controller is preferably self contained in a small package. For example, one such computer is the Basic Stamp™ (model I or II) manufactured by Parralax, Inc. FIG. 8 also shows the controller connected to a motor controller 58 which is in turn connected to a motor 59 for driving the propulsion mechanism 42, which in turn drives the track engagement mechanism through a drive mechanism (not shown), such as a set of gears or a pulley system.

Preferably, the controller 44 performs various functions, including moving forward, activating the micro positioning system, activating the robot identification process, operating the collision avoidance system, operating the error correction system, lighting or turning off indicator lamp(s), providing an audible signal via the speaker, etc. A benefit of autonomous navigation is that the proper movement of the robot between stations can occur within each individual robot device, so that each robot has a high dynamic range which keeps the cost of the system low and also allows scalability of the system. This also enhances the flexibility and versatility of the robot devices of the present invention.

Figure 11A:
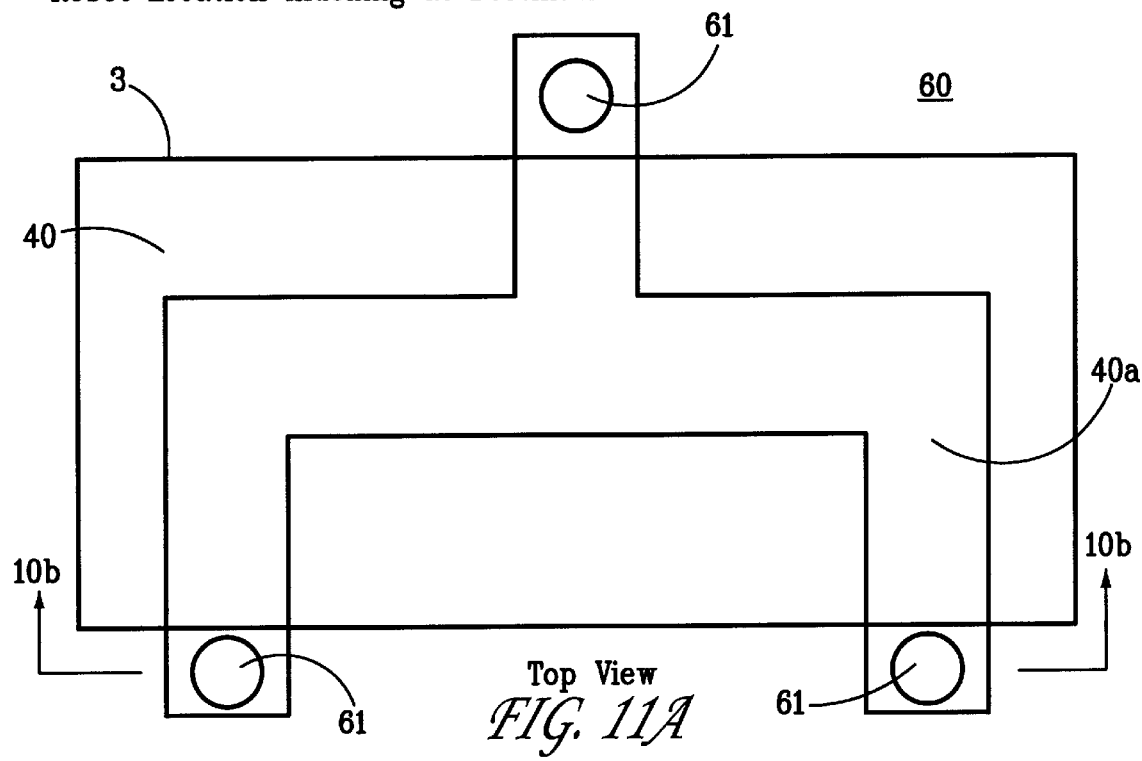
FIG. 11A is a top view of an exemplary robot micro positioning system in accordance with the present invention.
Figure 11B:
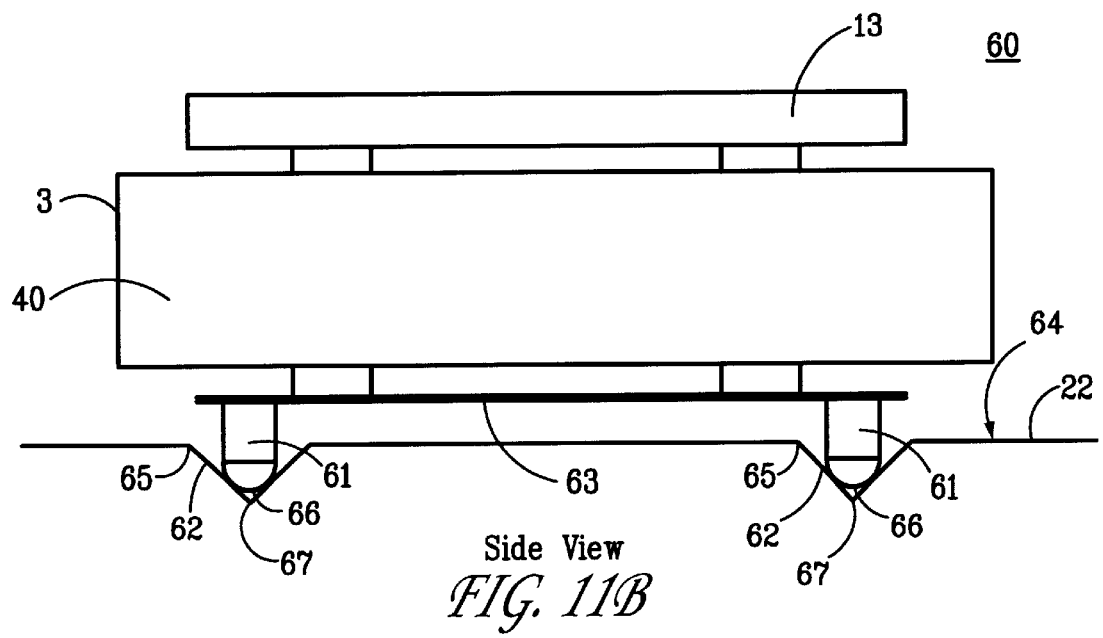
FIG. 11B is a side view of the micro positioning system of FIG. 11A.

FIGS. 11A and 11B show an exemplary micro positioning subsystem 60. The micro positioning subsystem 60 is disposed between the robot 3 and the station 4, or device. As shown in FIG. 9, when a robot 3 reaches its destination, it precisely locates itself in a predetermined location in space relative to the device 8 using the micro positioning subsystem 60. Preferably, the micro positioning system 60 includes a locating fixture 61 on the robot 3 and a cooperating locating fixture 62 at each station 4. In one preferred embodiment, the locating fixture 61 includes one or more projections, or feet, extending from an underside 63 of the robot body 40 and the cooperating locating fixture 62 includes one or more depressions, or recesses, formed in a top surface 64 of the working surface level 22 at a station.

Preferably the number and shape of the locating fixture 61 and the cooperating locating fixture 62 are coordinated to match one another. In addition, some tolerance is preferred between the top end 65 of the depression 62 and the distal end 66 of the projection 61, this tolerance allows for the gross positioning of the robot 3 with respect to the station 4 and device 8 and also assists in the locating, or lead-in, of the projections 61 into the depressions 62. It is also preferred to round, or taper, the edges of both the distal end 66 of the projections 61 and the top edge 65 of the depressions 62 openings in order to provide a smooth lead-in thereby assisting in the locating of the projections 61 into the depressions 62. Once the projections 61 are completely inserted into the depressions 62, the distal end 66 of each projection 61 and the bottom 67 of each depression 62 preferably form a tight clearance thereby providing for the precision positioning of the robot 3 with respect to the station 4 and device 8.

As shown in FIGS. 11A and 11B, this can be accomplished by the robot 3 lifting itself onto three hemispherical feet 61 attached to the robot body 40, preferably extending from an under surface 63 of the robot 3, such as the under surface of a sub-frame 40a. These projections 61 drop, engage, or fit into three conical-shaped depressions 62 formed in the top 64 of the working surface level 22 at the station 4 and under the robot 3. Preferably, these depressions 62 are indexed to the device 8 which will interact with the robot 3. Preferably, the sub-frame 40a is also the point of attachment for the plate or sample holding device 13.

This preferred micro positioning system 60 having three points of contact for micro positioning the robot acts to precisely locates the robot 3, and thus the plate 13, or sample device, in six degrees of freedom, relative to the device 8, allowing accurate manipulation of its samples 9, or cargo, depending on the station 4 the robot 3 is at. Preferably, the micro positioning system locates the sample 10× or better than the macro positioning system. For example, in an exemplary robotic system involving biometric samples contained in standard 96-well plates, the robot can be positioned near, for example, a pipette device, within about 5 mm to about 1 mm, and then the samples can be precisely located in a predetermined location in space with respect to the station to within about 0.5 mm to 0.1 mm or better.

Alternatively, the components of the micro position system 60 can be reversed, as between the robot 3 and the station 4. For example, the locating fixture 61 can include depressions formed in an undersurface 63 of the robot body 40, and the cooperating locating fixture 62 can include projections extending upward from the top 64 of the working level surface 22 proximate the station 4 and the device 8. In this embodiment, the robot 3 could lower itself onto the projections 61 such that the projections 61 fit within the depressions 62, or alternatively, a portion of the working surface could raise up, such as for example a piston actuated platform, to lift the robot or plate, thereby engaging the micro positioning system 60. In addition, other precision positioning devices can be used, such as, for example, G.P.S. positioning, laser and light positioning, acoustic positioning, magnetic positioning, etc.

Figure 11C:
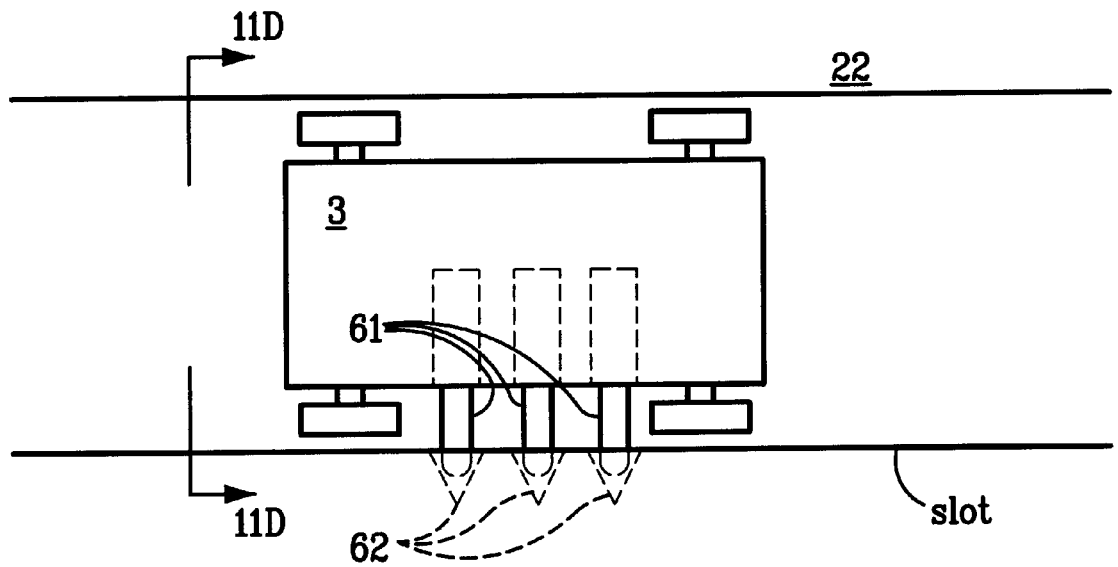
FIGS. 11C and 11D show another exemplary micro positioning subsystem.
Figure 11D:
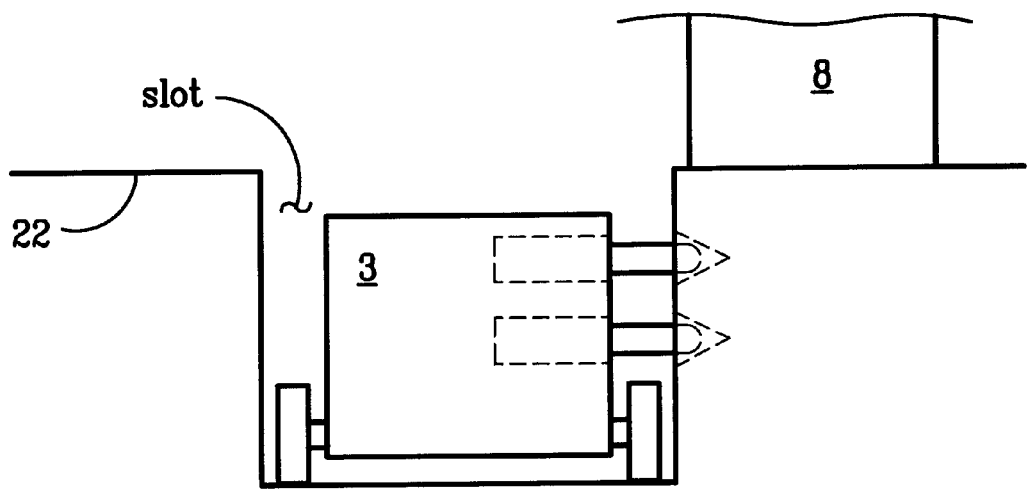

In addition, the micro positioning system 60 can be adapted based on the particular system and robot design for a given application. For example, in an embodiment having a robot in a channel, or slot, design, the micro positioning system could comprise one or more bars or rods that extend outward and cooperate with, for example, the side walls of the channel or slot, as shown in FIGS. 11C and 11D.

Figure 12:
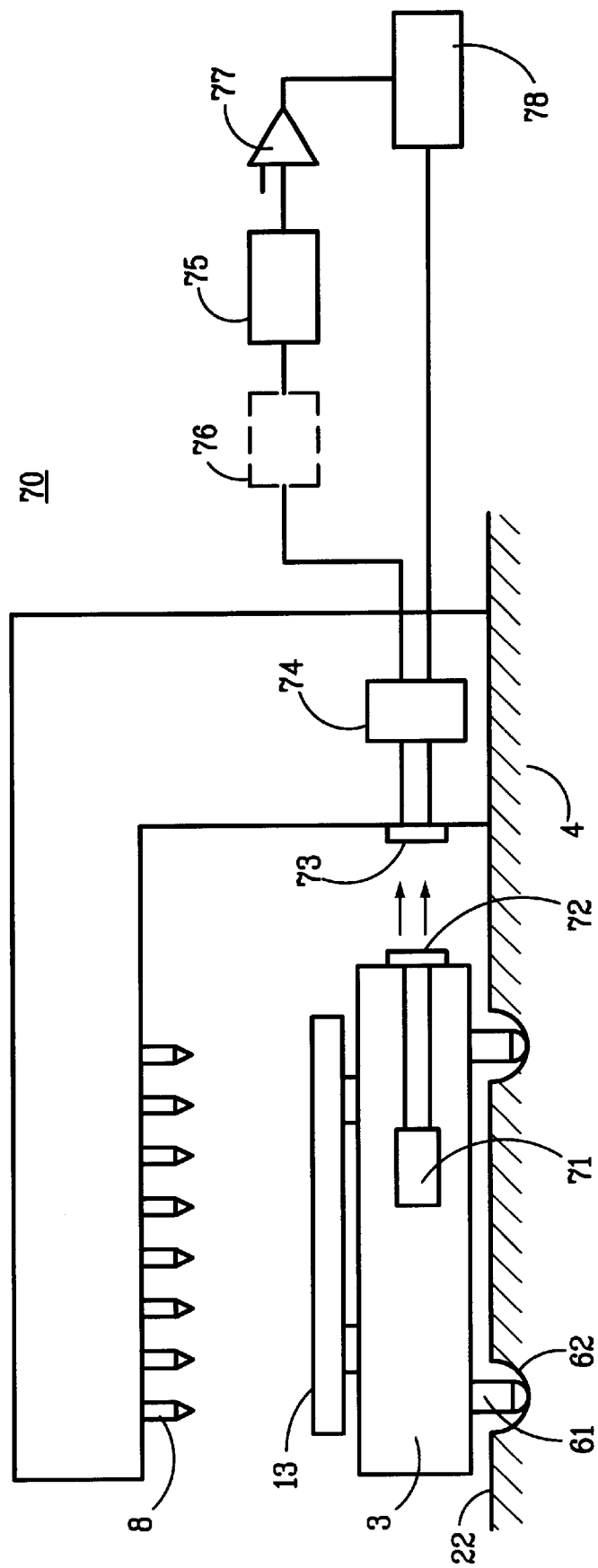
FIG. 12 is a block diagram of an exemplary robot identification and communication system in accordance with the present invention.

As shown in FIG. 12, the system can include an identification and communications system 70. Preferably, because it is desirable to keep the robots 3 simple and easy to manufacture, the robots 3 are constructed such that they do not require constant communications with the devices 8 or the central controller 30. However, in this type of embodiment, the robots 3 preferably provide for communications when they are docked at a station 4.

Preferably, when the robot 3 reaches its final destination (e.g., by detection of the last entry in the navigation instructions or binary list or by detection of a station) an attempt can be made to identify the robot 3 and to determine whether the robot 3 is at the correct location 4. Any known identification and communications technology can be used to identify the robot 3 and to determine if it at the correct location 4, including, for example, by-directional infrared link, short range RF, RFID, by electrical contact through the indexing feet 61, 1-D or 2-D bar code, etc.

An exemplary identification and communications system is shown in FIG. 12. As shown, the identification and communications system 70 is disposed between the robot 3 and the station 4 and/or device 8. As shown, the robot 3 includes an integrated circuit 71 having processing and memory functions disposed therein. The integrated circuit 71 can control an indicator device 72 disposed on an outer surface of the robot body 40. The station 4 or device 8 can include a sensor device 73 and an integrated circuit 74 having processing and memory functions disposed therein. The indicator device 72 illuminates or activates the sensor device 73.

Once the sensor device 73 has been activated, the microprocessor 31 at the central controller 30, or a similar system at the station 4, processes and compares the signal form the indicator device 72 to stored robot identification data stored in a memory. As shown, the integrated circuit 74 is coupled to a gain stage 75 through an optional filtering device 76. Gain is applied to the output of the sensor device 73 and the output from the gain stage 75 is provided to a comparator 77 which compares the received identification data with stored identification data. The results of the comparison are provided to a microprocessor 78 which determines if the robot 3 is at the correct location 4, and based on the comparison activates the device 8 or sends a new set of navigational instructions to the robot 3.

Several exemplary examples that can comprise the indicator device 72 and the sensor device 73 described herein above, include, for example, an LED indicator and a light sensor; an infrared indicator and infrared sensor; a communications port provided at both the robot and the station or device for establishing one of a wired and a wireless connection between the robot and the station; an imager/camera for capturing a graphical representation; an RFID tag having a transporter and a reader; an optical recognition system; a magnetic storage strip and reader, 1-D or 2-D bar code, an integrated chip or embedded memory chip, a key and corresponding slot, etc. Preferably, the indicating device 72 is located on the robot 3 and the sensing device 73 is on located at the station 4. An exemplary identification system that can be used with the present invention is the Infrared Proximity Detector Kit (IRPD) manufactured by LYNXMOTION, of Pekin, Ill. However, the location of the indicating device and a sensing device can be interchangeable as between the robot and station.

Once the identification of the robot 3 has been successfully completed, and it is determined that the robot 3 is at the correct location 4, the device 8 is activated and begins to interact with the robot 3 thereby performing some function or manipulation on the sample 9 contained in the sample holding device 13. For example, in an exemplary embodiment involving biometric samples contained in a 96-well plate, the robot is grossly positioned near, for example a pipette device (e.g., within about 5 mm to about 1 mm ) and then precisely located in a predetermined location in space with respect to the station 4 (e.g., within about 0.5 to about 0.1 mm or better), thereby virtually assuring that the sample 9 will be substantially centered or aligned with respect to the device 8. Under these conditions, the device 8 is activated and is free to perform some function on the sample 9, such as transferring, loading, unloading, monitoring, reading, accessing, etc. The devices themselves can communicate with each other and a central control system by standard networking technologies, such as TCP/IP. Note that the tolerance scale of the macro positioning system and micro positioning system is scalable with the rest of the system. For example, in a micro-robotic system, the tolerances may be even smaller, thereby keeping in scale with the rest of the robotic system.

Identification data can be stored on-board the robot 3 and transmitted to some type of sensor 73 on the station 4, or alternatively, the robot 3 can be a dumb device having some identifying feature that is read by the station and then compared to a stored identification characteristic in a memory of the station or a central database controlled by the central controller 30.

Optionally, the robot 3 of the present invention can be equipped with a passive feedback mechanism (not shown) which, for example, could be provided as an indicator or combination of indicators that provide, on a near real-time basis, an indication to an operator that the system is operating and functioning properly. For example, the feedback system might detect if a robot stops moving along the pathway, if a robot is moving the wrong way on the pathway, if a robot is lost, if a robot is not being positioned properly with respect to a device, etc.

In addition, the system can include position indicators (not shown) that show the location in the system of the robots. Preferably, the indicators are visible and/or audible, such as, an indicator lamp (e.g., a light emitting diode (LED)) that lights, for example, when a robot is lost, and an aural indicator via a speaker, such as a beep or other tone, that sounds periodically until the robot or an operator corrects the robot and puts it back on the correct pathway. Alternatively, a display device, such as a video display or an LCD, can be provided for viewing or displaying a status or condition of the system.

Referring back to FIG. 1, the system 1 includes one or more devices 8 for interacting with the robots 3. Devices 8 are components of the system that are preferably fixed in location, as shown in FIG. 12. Alternatively, a device 8 can be mounted on a robot 3 wherein the device 8 can be transported around the system 1 to interact with, for example a sample, or cargo, storage devices. Devices 8 can perform various functions, such as, for example, transferring liquid from one plate to another (with pipettes or transfer pins), reading some attribute of the sample like fluorescence or optical density, manipulating samples in some other way, etc. In all sample carrying robot embodiments discussed herein, these devices 8 are located at the destinations 4 that the robots 4 carry their samples 9 to.

Devices 8 access plates 13 holding samples 9 either in place on the robot, or by transferring them to the device by a simple pick and place arm (not shown) built with, for example, PWM servos or Nitinol thermally activated memory metals. This arm could be fixed relative to the device, or alternatively, the arm can be mounted on the robot itself. Optional lids on the plates (not shown) could be manipulated by the same pick and place arm, or by an arm on the robot itself, which would hold the lid out of the way during access.

Figure 13A:
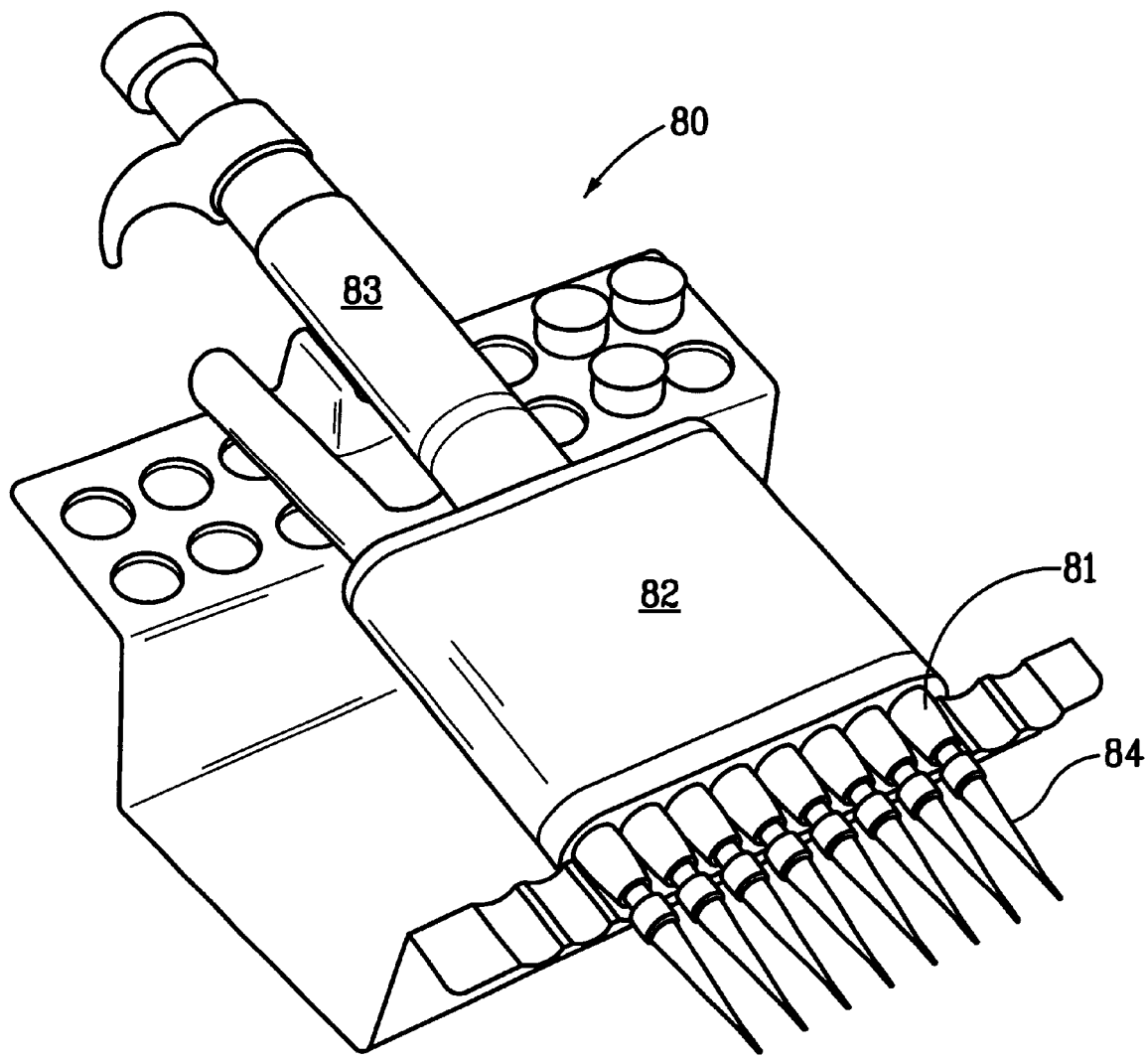
FIG. 13A is a schematic diagram of an exemplary device of the system of FIG. 1.
Figure 13B:
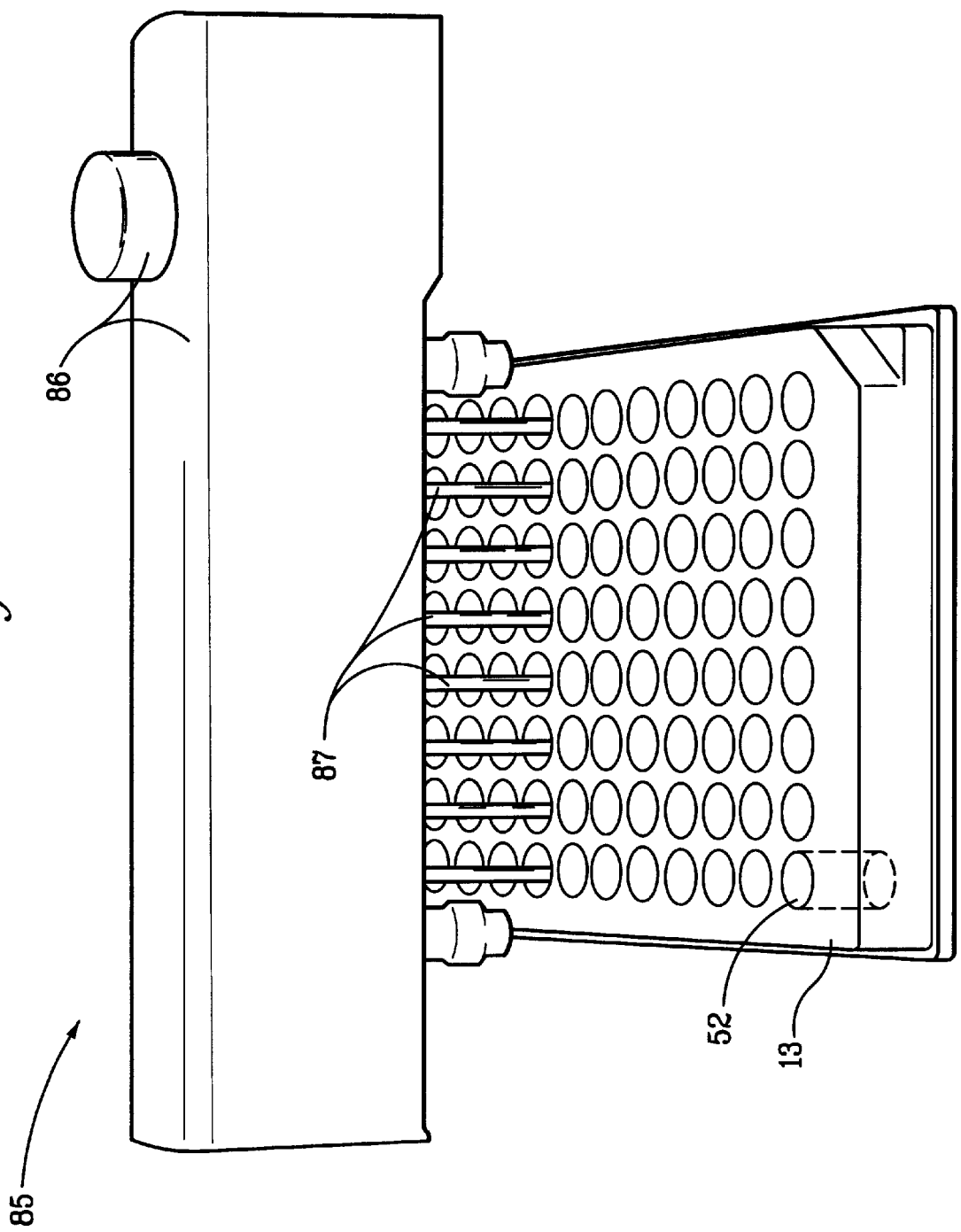
FIG. 13B is a schematic diagram of another exemplary device of the system of FIG. 1.

FIGS. 13A and 13B show exemplary devices 8 for an exemplary liquid handling system in accordance with the present invention. One or more devices 8 can be positioned at a station 4 for interaction with a sample 9 carried on the robot 3. Preferably there is one device 8 at each station 8, as shown in FIGS. 1 and 12, and the device 8 is adapted for the precision interaction with the robot 3.

For example, in an exemplary liquid handling system, an exemplary device 8 can be any standard device, including, for example, a plate washer device, a pipette device, a plate reader device, etc. The device 8 interacts by manipulating or performing some function on the samples 9. The device 8 can include any device for interacting with a sample 9 depending on the application. Each device 8 are designed for precision interaction with the samples 9 carried on the robot 3.

FIG. 13A shows an exemplary pipette device 80. As shown, the pipette's device 80 includes a plurality of pipettes having a body 81, a manifold 82, an actuator mechanism 83, and a tip 84. The pipette device 80 is activated once the robot 3 has been properly positioned and identified. The device 8 then interacts with the samples 9 to perform a preselected function or operation on the samples 9, such as filling, taking a sample, analyzing a sample, etc.

FIG. 13B shows an exemplary plate washer device 85. As shown, the plate washer device 85 includes a manifold 86 having a plurality of nozzles 87 extending therefrom. A washing agent (not shown) is sprayed from the nozzles 87 into the wells 52 of the sample holding device 13 to clean it. After the wash cycle is complete, the nozzles 87 can pull the wash agent from the wells 52 of the sample holding device 13.

The sample positioning system 1 of the present invention is preferably fast enough that significant plate 13 and sample 9 storage is required to feed the process and to incubate samples during the processes. Several potential means are available for this.

Figure 14:
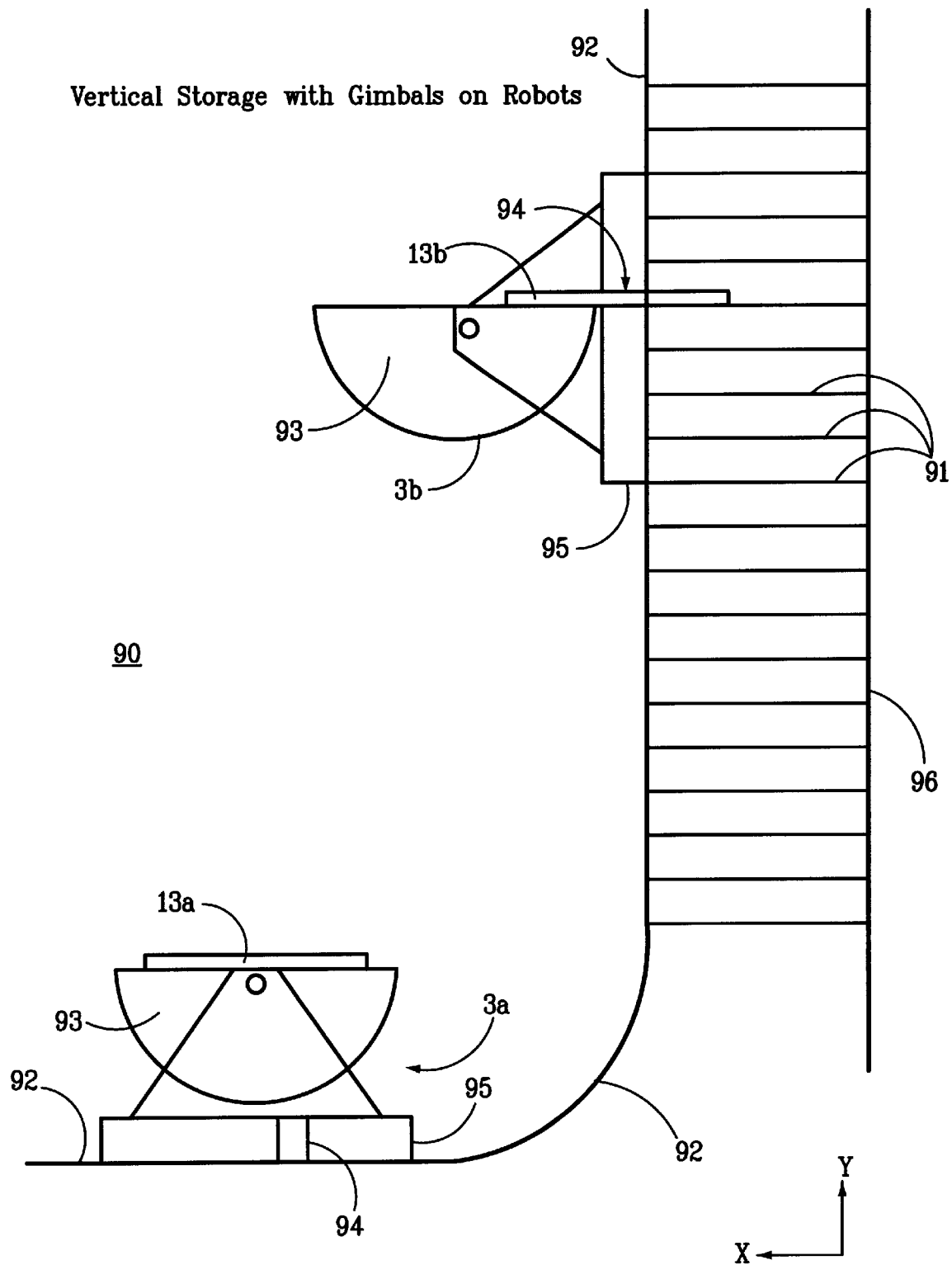
FIG. 14 is a schematic diagram showing an exemplary vertical storage device in accordance with the present invention.

As shown in FIG. 1 and FIG. 14, the system 1 can also include a storage system 90 for the storage of various cargo and samples 9. The storage system can be oriented horizontally (e.g., along the X-axis), as shown in FIG. 1, or alternatively, the storage system can be oriented vertically (e.g., along the Y-axis), as shown in FIG. 14.

As shown in FIG. 14, samples are stored in one or more storage devices 91 located on levels which are preferably positioned close together one on top of the other (e.g., vertically). The storage devices 91 can comprise any standard storage mechanism, such as for example shelves, racks, bins, containers, etc. These shelves 91 are supported by a support structure 96.

The support structure 96 can also supports a track 92. A robot can run on this track 92 both horizontally, as shown by robot 3a, and vertically, as shown by robot 3b. As shown, the robot has a gimbaled platform 93 for the plate 13a, 13b to rest upon. Robot 3a shows the gimbal 93 in the horizontal position, while robot 3b shows the gimbal in the vertical position. In the vertical case, the plate 13b is still level and can be slid into or out of a shelf 91 through an opening 94 formed in the base 95 of the robot 3.

The robot 3 can be made to run vertically by several means. For example, if the robots 3 are very small, simple magnetic attraction to the track 92 will normally be sufficient. Larger robots may require a track gripping mechanism, such as for example, a cog rail, pins, rods, hooks, etc. for gripping the track.

In an alternative embodiment (not shown), the storage locations can be arranged in shelves with tracks running between shelves on each level. The robots get to the desired level for drop off or pick up by navigating up ramps, such as for example a spiral ramp. Each turn of the spiral raises the track to the next shelf. At each turn a standard forking intersection is reached, which the robot navigates in the usual style. Thus, storage locations are like any other device. Plates or samples can be loaded or unloaded from the robots by, for example, an arm built into either the robot or the storage location which sweeps the plate from the robot storage location, or vice versa. This arm does not need proportional control and could be actuated by Nitinol or solenoid. Similar downward traveling ramps can also be provided.

The robotic positioning system of the present invention can also include an error recovery system. For example, all stations, or destinations, can be marked with a separate sensor. When a robot arrives at what it thinks is its destination, it announces itself and its sample ID to the station. The station can be told to expect a certain list of samples. If the station is expecting this sample, in addition to performing its operation, it gets navigation instructions for the robot's next task from central control and passes these to the robot. If it is not expecting this sample, it checks with central control and gets new navigation instructions for the robot which lead it from wherever it ended up in error to the correct location in the system. It gives the robot these instructions and sends it on its way.

If communication fails or the robot is not identified for some other reason, the robot assumes that it is lost and can follow its emergency instructions. These instructions can, for example, be a simple set of instructions that direct the robot to stop at all future intersections to see if they are devices which it can communicate with. If the intersection has no device, it makes, for example, a left turn and continues to the next intersection. As soon as it finds any device with which it can communicate, that device requests new navigation instructions from a central control on behalf of the lost robot. Alternatively, if the robot is not identified, it can activate an indicator and an operator could be notified to place the robot back onto the correct pathway.

Figure 15:
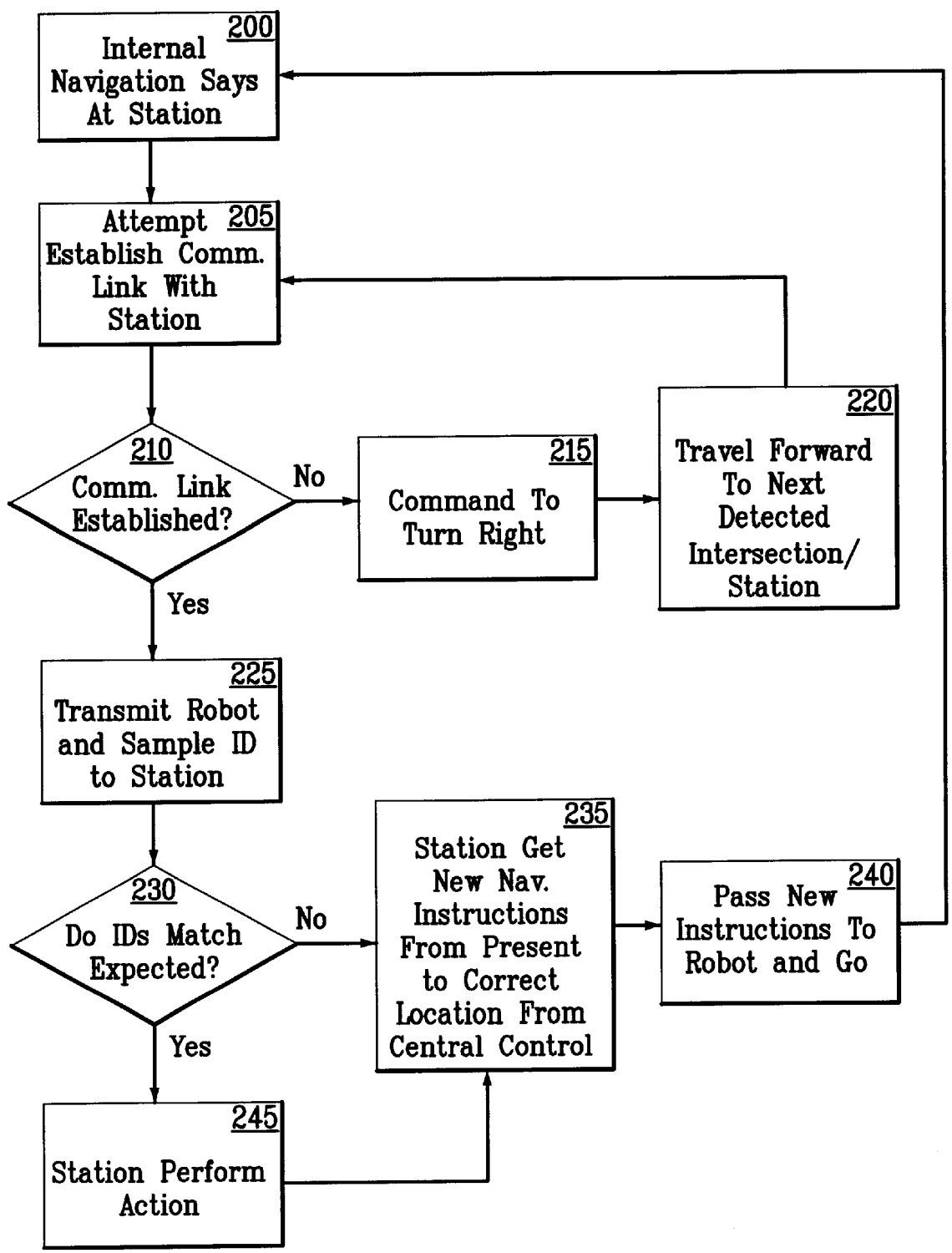
FIG. 15 is a flow chart of an exemplary method of robot identification and error correction in accordance with the present invention.

FIG. 15 is a flowchart showing an exemplary robot identification process with error correction. As shown in FIG. 15, the internal on-board computer indicates that the robot is at a station, or destination, at step 200. The robot then attempts to establish communications with the station, at step 205. The robot determines whether a communications link has been successfully established at step 210. If it is determined, at step 210, that no communications link is established, then the robot executes a default set of navigational instructions and turns right, at step 215. The robot then travels forward at step 220, to the next station/intersection is detected, at which time the robot again attempts, at step 205, to establish a communications link with the station.

If it is determined that a successful communications link was established, at step 210, then the robot transmits its own identification to the station, at step 225 for identification. The robot can also transmit an identification code of the cargo or sample that it is carrying to the station, at step 225. The station then determines whether the identifications of the robot and/or the sample match an expected identification code, at step 230. The stored identification codes can be stored in a memory at the station or in a central database.

If the identification codes do not match at step 230, then the station can get new navigational instructions from the central controller, at step 235 and passes/loads these new instructions into the robot and the robot moves forward, at step 240, in order to attempt to correct the location of the robot. The robot continues forward until its on-board navigational system again indicates that it is at a station, at step 200. If the identification codes do match at step 230, then the station interacts with the robot, at step 245, such as performing some action or functions on the cargo, or samples. Once the station has completed its interaction with the robot at step 245, the process proceeds to step 235, 240 and then 200 as described herein above.

The system of the present invention can include a collision avoidance system 165. The collision avoidance system 165 acts to prevent the robots 3 from colliding with one another as they move around the pathways 5. The collision avoidance system 165 can be disposed between individual robots 3, or alternatively, it can be disposed between the robots and a position along the pathways 5, such as proximate an intersection 10 and/or a station 4.

The collision avoidance system 165 can include an indicator or transmitter device 166, a sensor or receiver device 167, and an integrated circuit 168 having processing and memory functions disposed therein. The indicator 166 and sensor 167 can be any standard type of compatible indicator device and sensor device, including, for example, an optical system, an acoustic system, an electromagnetic system, an electrical system, a RF system, etc. Although not required, it is preferred that the collision avoidance be handled locally by the individual robots, thereby not requiring a central control management for the tracking of detailed position and prevention of collisions.

FIGS. 16A, 16B, 17A and 17B show exemplary collision avoidance systems 165 designed to prevent one robot from colliding with another robot. The collision avoidance systems 165 preferably at least accounts for potential collisions at merging pathways in the system and for rear-end collisions.

Figure 16A:
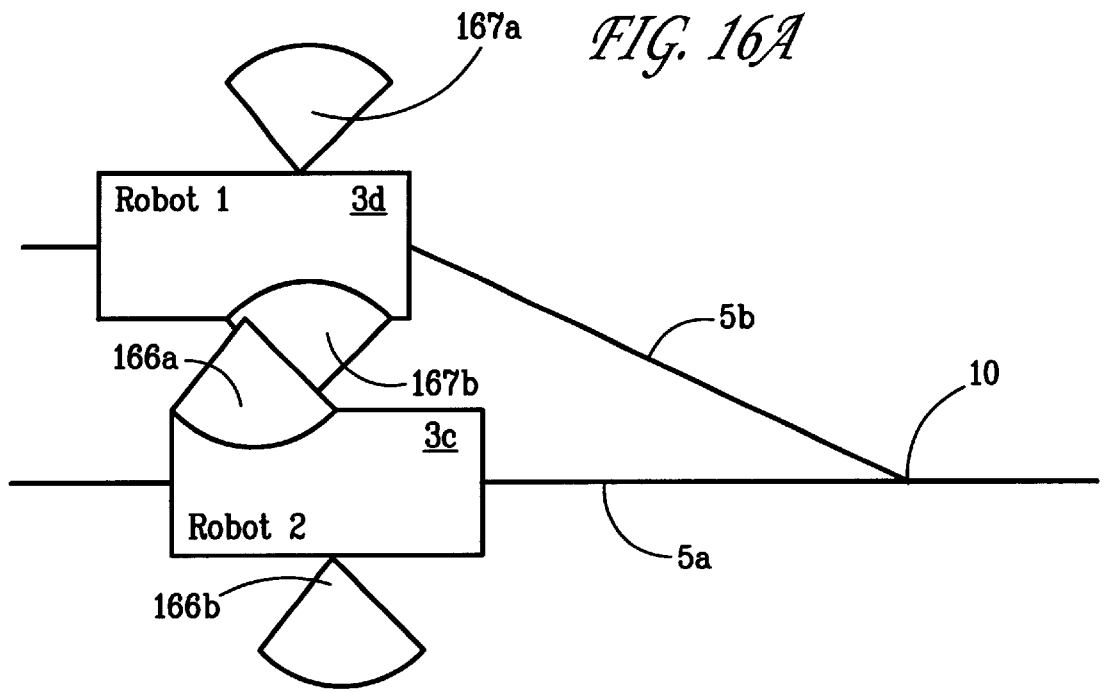
FIGS. 16A and 16B are schematic diagrams showing an exemplary track merger collision avoidance system in accordance with the present invention.
Figure 16B:
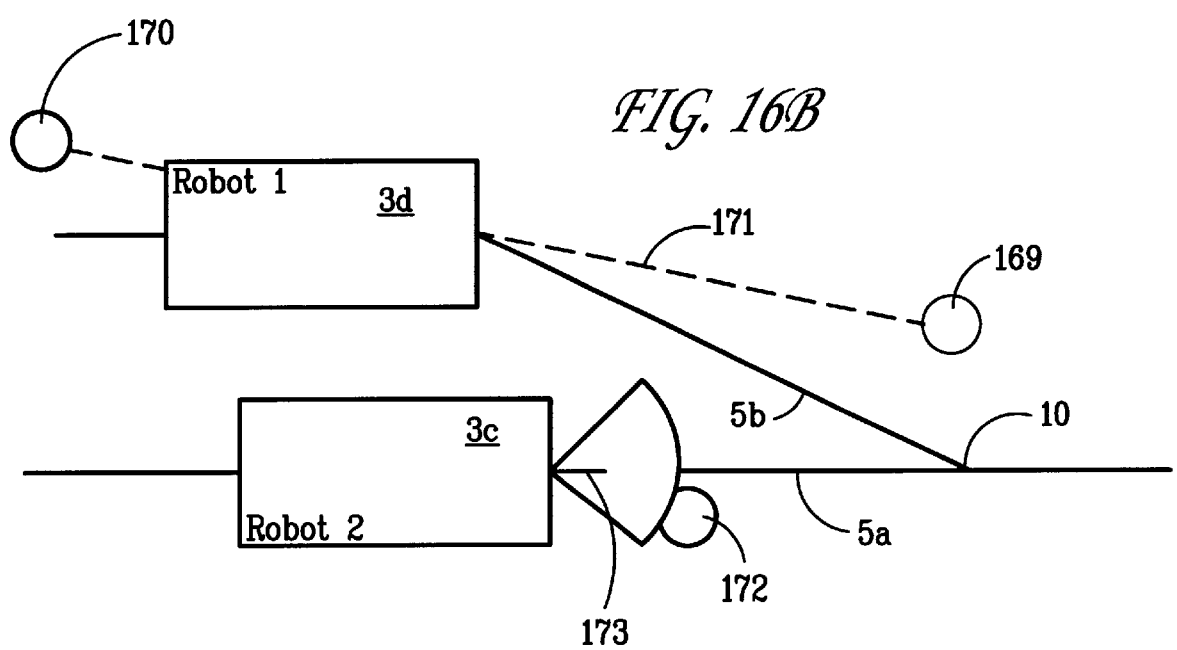

For example, FIGS. 16A and 16B show several exemplary embodiments of collision avoidance systems 165 for merging pathways. In a first track merger collision avoidance system shown in FIG. 16A, each robot can have one or more indicator device 166, such as, for example, an IR LEDs, positioned on the right side of the robot body 40 pointing out to the right (166a and 166b of FIG. 16A). Each robot can also have a detector device 167, such as, for example, an IR sensor, positioned on the left side of the robot body 40 pointing to left (167a and 167b of FIG. 16A). If a robot's left looking sensor 167a, 167b is activated, it assumes that another robot is approaching an intersection 10. In this embodiment, the detecting robot slows or stops until the signal clears, thus allowing the robot on its left side to have the right of way. As shown in FIG. 16A, robot 3c is on pathway 5a on the right and Robot 3d is on pathway 5b on the left. Robot 3c stops, or slows, because its sensor 167b sees robot 3d's indicator 166a. Parallel paths with traffic moving in opposite directions do not cause a problem because the robots pass either indicator to indicator or sensor to sensor, causing no detection. Problems with parallel paths moving in the same direction can be avoided by providing a barrier (not shown) to block the sensor from the indicator, by separating the parallel pathways by a sufficient distance to avoid sensing of the indicator, or alternatively, The robot on the left will stop or slow momentarily until the robot on the right travels down its pathways and is no longer detected.

FIG. 16B shows another track merger collision avoidance system. As shown in FIG. 16B, the collision avoidance system 165 can include, for example, electronic devices 169, 170 disposed along the left side of one or more of the pathway 5a, 5b. As shown, the electronic devices 169, 170 can include, for example, an IR LED indicator 169 and a receiver 170 pair disposed across path 5b to detect the presence of robot 3d. Robot 3d is detected by the robot 3d blocking or interrupting, for example a light path 171 between indicator 169 and sensor 170. When a robot 3d is detected on the left fork 5b as shown, the electronics can illuminate an indicator 172, such as an LED, positioned along the right fork 5a pointing toward any oncoming robots, such as robot 3c shown. If a robot does come down that right path 5a, a rear-end collision detection sensor 173 disposed on the front of the robot 3c can be activated causing robot 3c to stop, thinking it is about to hit a robot from behind. Robot 3c remains stopped until indicator 172 is turned off, which only happens when the other robot 3d clears the left fork 5b, as indicated by light path 171 being re-established between indicator 169 and sensor 170.

An exemplary rear-end collision avoidance system 165 is shown in FIGS. 17A and 17B. As shown in the exemplary system of FIGS. 17A and 17B, rear-end collision avoidance can be accomplished by positioning an indicator device 175, such as an IR LED, on the rear of each robot body 40 and positioning one or more sensor devices 176a, 176b, such as IR sensors, on the front of each robot body 40. This embodiment can provide multiple distance warnings.

In FIG. 17A the robot is at medium distance and sensor 176a can detect LED 175 through a pinhole opening 177, as illustrated by beam line 178a. Robot 3d slows down in response to this signal. In FIG. 17B, robot 3d is at close range allowing sensor 176b to detect LED 704. In response to this signal, robot 3d stops, or slows further. Multiple levels and even analog ranges are possible to measure by extending this system. In addition, this system can also be used by the track itself, for merging collision avoidance, or alternatively by a device along the track to stop a robot.

Figure 18:
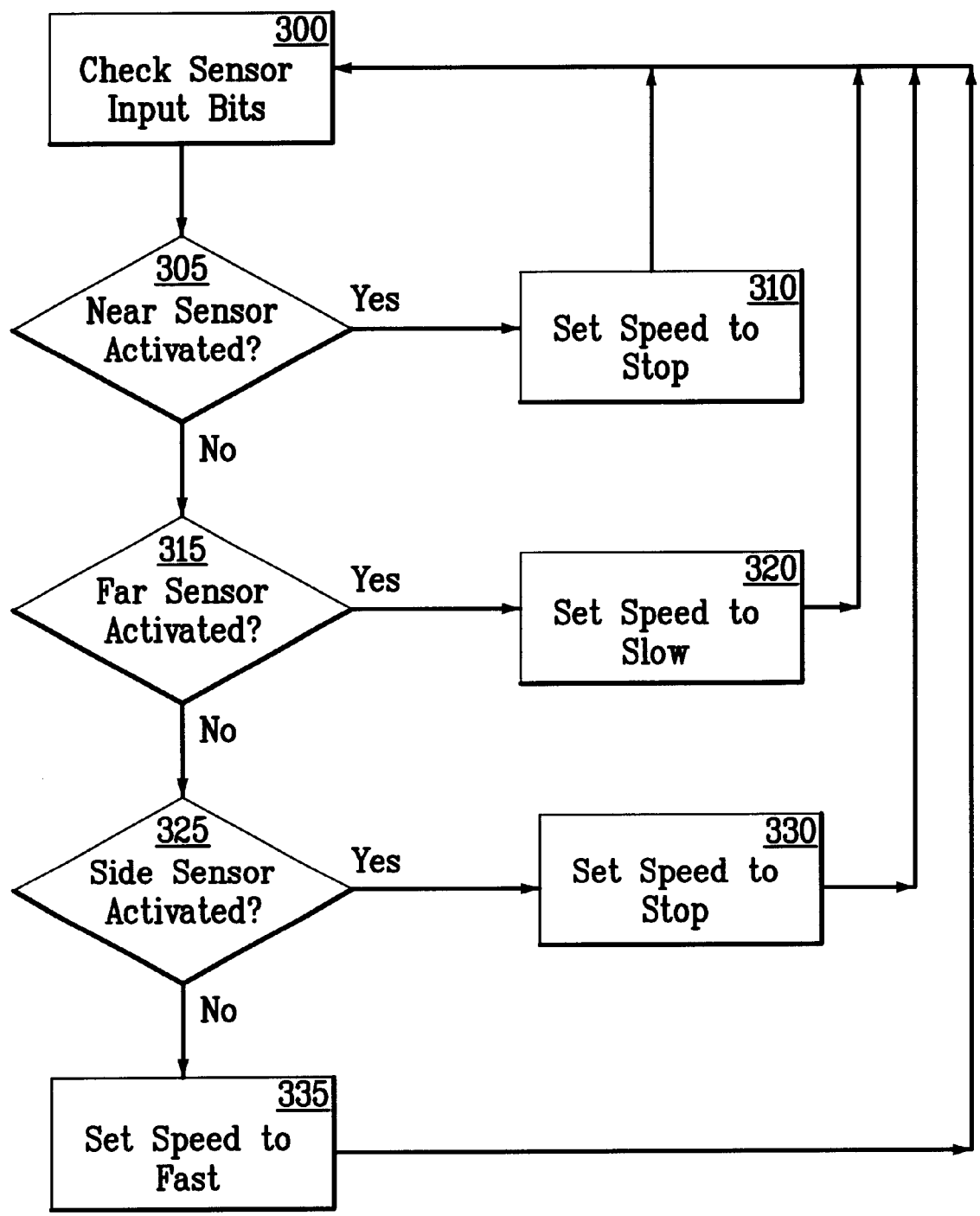
FIG. 18 is a flowchart of an exemplary method of side and rear-end collision avoidance in accordance with the present invention.

FIG. 18 is flowchart combining the exemplary merging pathways collision avoidance system of FIGS. 16A and 16B and the exemplary rear-end collision avoidance system of FIGS. 17A and 17B. As shown in FIG. 18, the electronics check the sensor input bits, at step 300. At step 305 it is determined whether or not the near sensor has been activated. If it is determined, at step 305, that the near sensor has been activated, then the electronics set the speed to stop, at step 310. After a predetermined period of time, the electronics again check the sensor input bits, at step 300.

If it is determined that the near sensor has not been activated, then the electronics proceed to step 315, where it is determined whether or not the far sensor has been activated. If it is determined, at step 315, that the far sensor has been activated, then the electronics set the speed to slow, at step 320. After a predetermined period of time, the electronics again check the sensor input bits, at step 300.

If it is determined, at step 315, that the far sensor has not been activated, then the electronics proceed to step 325, where it is determined whether or not the side sensor has been activated. If it is determined, at step 325, that the side sensor has been activated, then the electronics set the speed to stop, at step 330. After a predetermined period of time, the electronics again check the sensor input bits, at step 300.

If it is determined, at step 325, that the far sensor has not been activated, then the electronics proceed to step 335, where the electronics set the speed of the robot to fast. After a predetermined period of time, the electronics again check the sensor input bits, at step 300.

The grid-type track system, described herein above with reference to FIG. 3, can have a different overall collision avoidance system (not shown) then the embodiments described herein above. The rear-end avoidance system can be identical to the system describe herein above with reference to FIGS. 17A and 17B, but front-end and side collisions can be handled differently.

Figure 19:
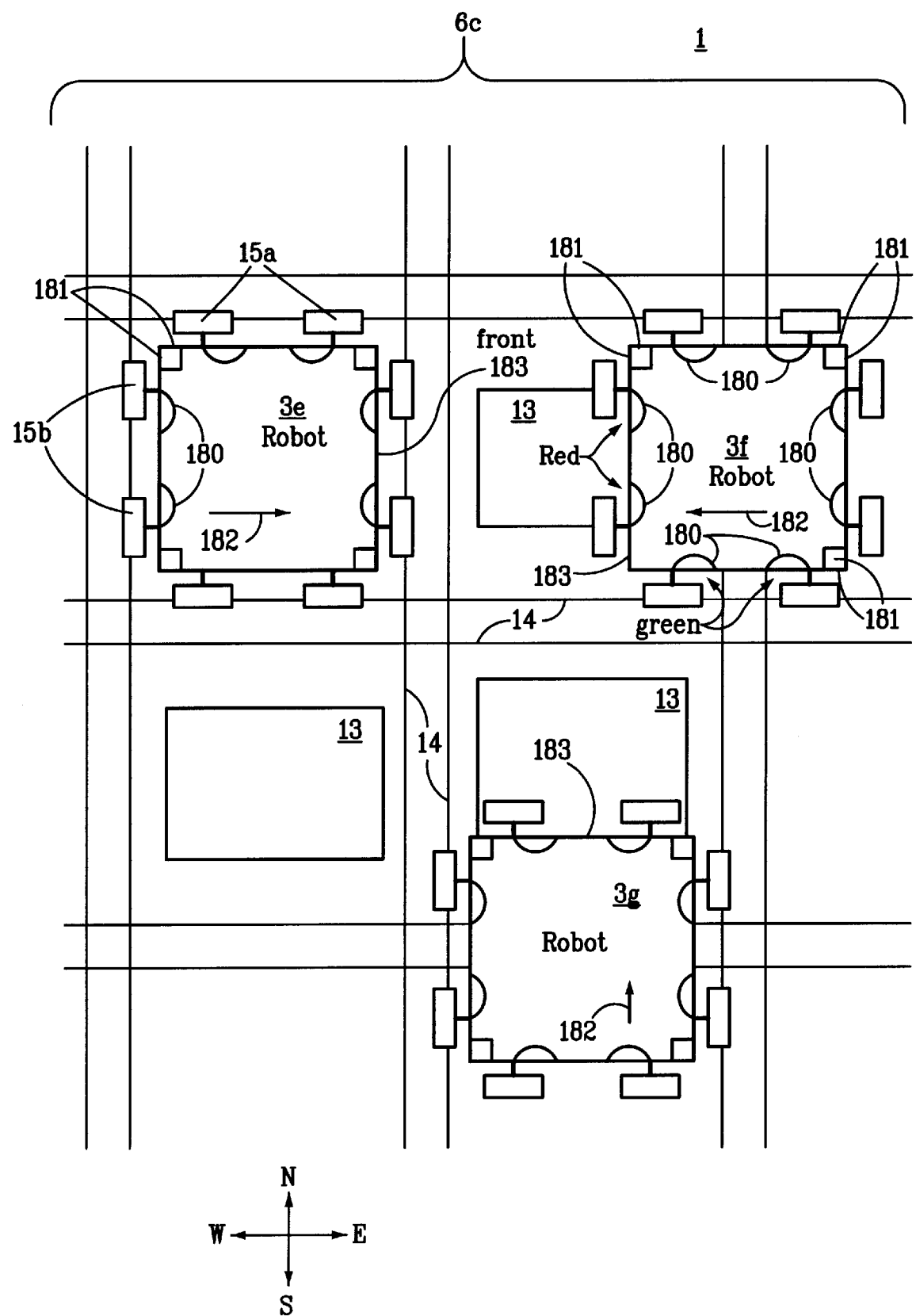
FIG. 19 is a schematic diagram of another exemplary collision avoidance system in accordance with the present invention.

FIG. 19 shows an exemplary collision avoidance system for use with a grid-type track system 6c. As shown in FIG. 19, each robot 3 can be configured with one or more computer controlled indicators 180, such as, for example, colors of LEDs, positioned on all four sides of the robot body 40, as well as one or more sensors 181 that can distinguish between these colors. Preferably, the sensors 181 are aligned such that they cannot see further than about one grid block, or alternatively, the indicators can only project out than about one grid block. In addition, preferably two indicators and two sensors are disposed on each side and are located at opposite ends of each side. A robot's "front" 183, as used here, always means the leading side in the direction of travel.

For example, if a robot 3f is heading West, as indicated by directional arrow 182, the West side is the front 183. Robots control their lights such that the "front" light is always a first color, for example red, and the "side" lights are a second color, for example green. The "back" lights are preferably a third color and a separate system, as described in the rear-end collision avoidance section and shown in FIGS. 17A and 17B.

The collision avoidance technique used by all robots is preferably designed having a protocol that gives right-of-way to predetermined directions of traffic, such as for example, north and west bound robots. For example, the following rules can be used:

If moving North and see red, go straight;

If moving South and see red, turn West for one block;

If moving West and see red, go straight;

If moving East and see red, turn North for one block; and

If see green, stop until green is gone.

Using the above exemplary protocol for the robots 3e, 3f, and 3g of FIG. 19 would yield the following results. Robot 3e, which is shown traveling East, would see the red lights of robot 3f, which is shown traveling West. Accordingly, robot 3e would turn north for one block. Robot 3f would also see the red lights of robot 3e and since it is traveling West, robot 3f would continue to travel straight (e.g., West). Robot 3g, which is shown traveling North, would see the green lights of robot 3f, which is again traveling West. Accordingly, robot 3g would stop until it no longer sensed the green lights of robot 3f.

Figure 20:
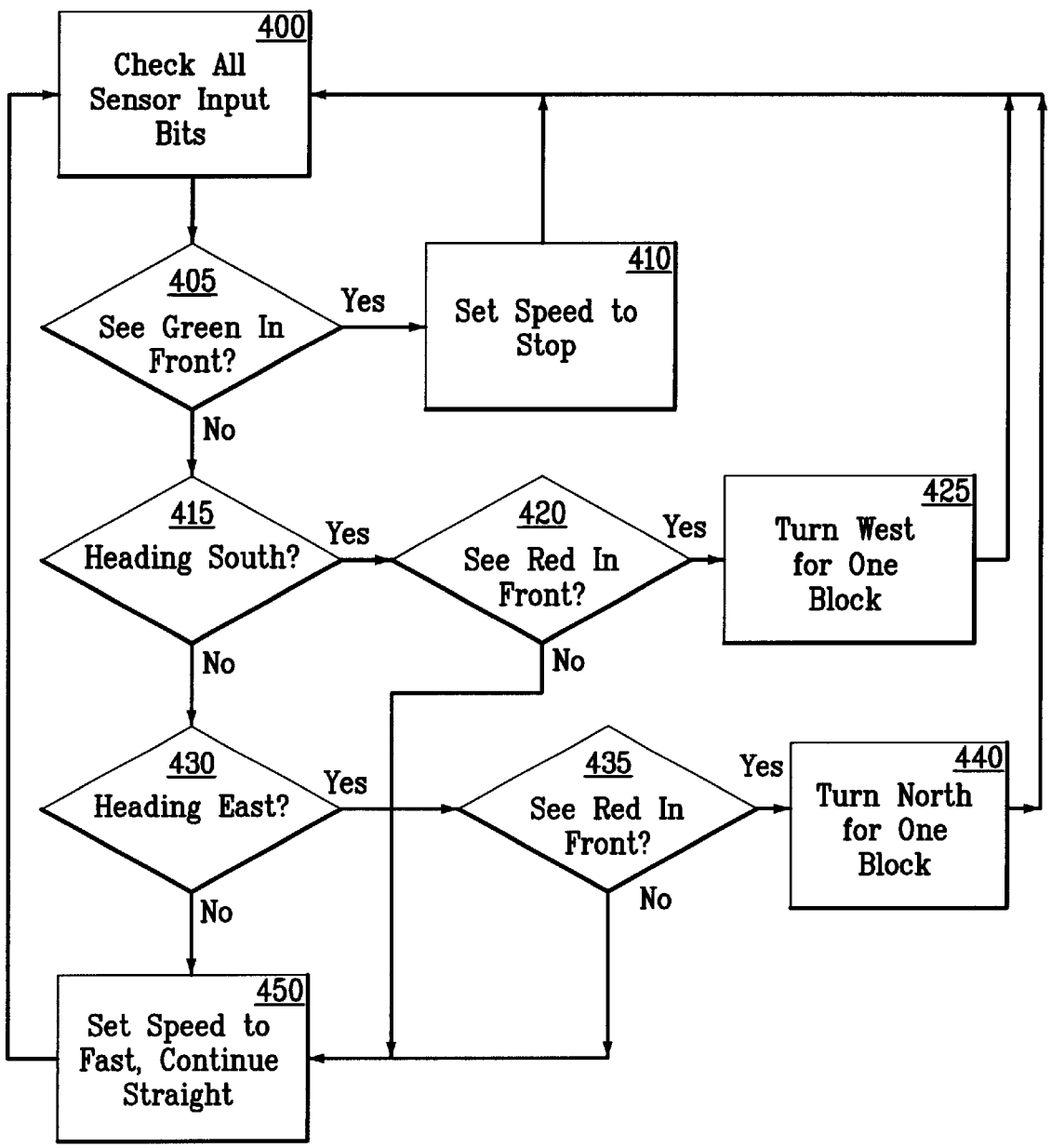
FIG. 20 is a flow chart of another exemplary method of collision avoidance in accordance with the collision avoidance system of FIG. 19.

FIG. 20 is a flowchart of the exemplary side and front collision avoidance system of FIG. 19. As shown in FIG. 20, the electronics check all sensor input bits, at step 400. At step 405 it is determined whether or not the sensor detects the color green in front. If it is determined, at step 405, that the color green has been detected, then the electronics set the speed to stop, at step 410. After a predetermined period of time, the electronics again check all sensor input bits, at step 400.

If it is determined that the color green has not been detected, then the electronics proceed to step 415, where it is determined whether or not the robot is heading South. If it is determined, at step 415, that the robot is heading South, then it is determined whether or not the sensor detects the color red in front, at step 420. If it is determined, at step 420, that the color red has been detected, then the robot turns West for one block, at step 425. After a predetermined period of time, the electronics again check all sensor input bits, at step 400.

If it is determined, at step 420, that the color red has not been detected, then the electronics set the robot speed to fast and continues the robot straight (e.g., in the same direction that it was traveling), at step 450. The robot continues to travel straight for a predetermined period of time, and then the electronics again check all sensors at step 400.

If it is determined, at step 415, that the robot is not heading South, then the electronics proceed to step 430, where it is determined whether or not the robot is heading East. If it is determined, at step 430, that the robot is heading East, then it is determined whether or not the sensor detects the color red in front, at step 435. If it is determined, at step 435, that the color red has been detected, then the robot turns North for one block, at step 440. After a predetermined period of time, the electronics again check all sensor input bits, at step 400.

If it is determined, at step 435, that the color red has not been detected, then the electronics set the robot speed to fast and continues the robot straight (e.g., in the same direction that it was traveling), at step 450. The robot continues to travel straight for a predetermined period of time, and then the electronics again check all sensors at step 400.

If it is determined, at step 430, that the robot is not heading East, then the electronics proceed to step 450, where the electronics set the robot speed to fast and continues the robot straight (e.g., in the same direction that it was traveling). After a predetermined period of time, the electronics again check all sensor input bits, at step 400.

The present invention comprising a system and method of accurately positioning a sample to be worked on or manipulated using a macro positioning subsystem and a micro positioning subsystem in a robotic system, has significant value in those situations where there are compelling needs for the gross movement and locating of samples between various stations coupled with the need for precision locating of the sample at each station with respect to a device at each station.

Although illustrated and described herein with reference to certain specific embodiments, it will be understood by those skilled in the art that the invention is not limited to the embodiments specifically disclosed herein. Those skilled in the art also will appreciate that many other variations of the specific embodiments described herein are intended to be within the scope of the invention as defined by the following claims.

What is claimed is:

1. A positioning system for automated sample movement and positioning comprising:
    a macro positioning subsystem for moving one or more transporters carrying a sample between stations having a device for interacting with said sample, said macro positioning system comprising:
        a predetermined track system connecting said stations;
        a plurality of self-propelled transporters disposed along said track system for carrying said sample between said stations, each of said plurality of transporters having an on-board propulsion system for moving each of said transporters along said track system;
        an on-board navigational system for controlling the movement of each of said transporters along said track system; and
    a micro positioning subsystem comprising a first locating structure and a cooperating second locator structure;
    wherein said first locating structure and said cooperating second locator structure comprise at least three points of contact disposed between said transporters and said station for locating said transporters with respect to said station, and thus said sample with respect to said device, thereby allowing accurate interaction of said device with said sample.

2. The positioning system of claim 1, wherein said track system further comprising one or more sidings, wherein said plurality of transporters running on said track system and said sidings comprise a queuing system which allows one or more transporter to wait on one of said one or more sidings at one of said stations while other transporters are allowed to continue to move between stations along said track system.

3. The positioning system of claim 1, further comprising a controller disposed on-board each of said plurality of transporters for controlling said navigational system.

4. The positioning system of claim 1, wherein said micro positioning subsystem comprises:
    said first locating structure on said transporter; and
    said second locating structure on said station for cooperating with said first locating structure to precisely locate said transporter and thus said sample with respect to said device at said station.

5. The positioning system of claim 1, wherein said first locating structure comprises at least three projections on said transporter and said second locating structure comprises at least three recesses in said station, wherein said projections cooperate with said one or more recesses to locate said transporter with respect to said device.

6. The positioning system of claim 1, wherein said first locating structure comprises at least three recesses on said transporter and said second locating structure comprises at least three projections on said station, and wherein said projections cooperate with said one or more recesses to locate said transporter with respect to said device.

7. The positioning system of claim 1, wherein said first locating structure comprises three projections and said second locating structure comprises three recesses, and wherein said three points of contact are arranged in a triangular pattern.

8. The positioning system of claim 1, wherein said first locating structure and said second locating structure extend in a direction substantially perpendicular to a plane defined by a working surface of said station.

9. The positioning system of claim 1, wherein said first locating structure and said second locating structure extend in a direction substantially parallel to a plane defined by a working surface.

10. The positioning system of claim 1, wherein said track system is a stationary track system comprising one of a rail follower system, a line follower system, a slot follower system, a light follower system, a magnetic follower system, and a channel follower system.

11. The positioning system of claim 1, further comprising a controller disposed on-board each of said plurality of transporters for controlling said navigational system, wherein said transporter provides for autonomous navigation of said transponder between said one or more stations.

12. The positioning system of claim 1, wherein said transporter further comprises:
    a body;
    a track engagement mechanism for engaging said track system;
    a sample holding device disposed on said body for holding said sample;
    an on-board controller for executing one or more navigational instructions;
    a memory for storing said navigational instructions;
    a propulsion mechanism for propelling said transporters along said track system; and
    a power supply for driving said propulsion mechanism.

13. The system of claim 1 further comprising an error correction system and a collision avoidance system controlled on-board said transporter, wherein said error correction system corrects a positioning of a lost robot along said track system and wherein said collision avoidance system provides for avoidance of a side collision and one of a rear-end collision and a front-end collision.

14. The system of claim 13 wherein said error correction system further comprises an error recovery instruction stored on-board said transporter and executed by an on-board controller.

15. The system of claim 13 wherein said collision avoidance system further comprises at least one indicator and at least one sensor disposed on each transporter and controlled by a controller on-board each of said transporters.

16. The system of claim 15 wherein said at least one indicator and said at least one sensor further comprise a side collision avoidance indicator and a side collision avoidance sensor and one of a front collision avoidance indicator and a front collision avoidance sensor and a rear collision avoidance indicator and a rear collision avoidance sensor.

17. The system of claim 1 wherein said micro positioning subsystem positions said sample with respect to said device to a magnitude of about 10 times or better than said macro positioning subsystem.

18. The system of claim 1 wherein a gross positioning of said transporter by said macro positioning subsystem is reproducibly in register at each of said stations to an accuracy of about 5 mm.

19. The system of claim 1 wherein a gross positioning of said transporter by said macro positioning subsystem is reproducibly in register at each of said stations to an accuracy of about 1 mm.

20. The system of claim 1 wherein a precision positioning of said sample carried by said transporter by said micro positioning subsystem is reproducibly in register with respect to said device at each of said stations to an accuracy of 0.5 mm.

21. The system of claim 1 wherein a precision positioning of said sample carried by said transporter by said micro positioning subsystem is reproducibly in register with respect to said device at each of said stations to an accuracy of 0.1 mm.

22. A method for moving and positioning samples in a robotic system comprising:
  providing predetermined pathways connecting one or more stations;
  disposing one or more sample carrier transporters along said pathways;
  activating a propulsion and navigation system located on each of said transporters to move each of said transporters along said pathways to a predetermined station;
  macro positioning each said transporters with respect to one of said stations;
  activating a micro positioning system disposed between said transporter and said station;
  micro positioning a sample on said transporter with respect to a device at said station using a first locating structure and a second locating structure comprising at least three points of contact disposed between said transporter and said station; and
  performing a function on said sample using said device.

23. The method according to claim 22, further comprising providing a track system connecting said stations thereby defining said predetermined pathways.

24. The method according to claim 22, further comprising identifying said transporter at said station as a transporter to be worked on by said device using an identification system disposed between said transporter and said station.

25. The method according to claim 22, further comprising deactivating said micro positioning system once said device has completed interacting with said sample, and continuing said movement of said transporter along said pathways.

26. The method according to claim 22, further comprising avoiding collision between said transporters using a collision avoidance system-disposed between one of said sample carrier transporters and said sample carrier transporters and said pathways.

27. The method according to claim 26, further comprising avoiding one or more of a side collision, a rear-end collision, and a front collision using one or more indicator devices and one or more sensors to indicate and sense a transporter position relative to another transporter.

28. The method according to claim 22, further comprising establishing a communications link between said transporter and said station and exchanging identification data and navigational instructions between said transponder and said station using said communications link.

29. The method according to claim 28, further comprising identifying said transporter as being a registered transporter for interaction with a device at said station using an identification system disposed between said transporter and said station.

30. The method according to claim 22, further comprising correcting errors in the location of said transporters at a station or within said system using an error recovery system.

31. The method according to claim 30, further comprising one or more of loading a set of default instructions from said on-board controller and loading a new set of navigational instructions from one of said stations using said error recovery.

* * * * *